United States Patent
Seifert et al.

(10) Patent No.: US 10,118,027 B2
(45) Date of Patent: Nov. 6, 2018

(54) OPEN CHANNEL IMPLANT TOOLS HAVING AN ATTACHMENT FEATURE AND IMPLANT TECHNIQUES UTILIZING SUCH TOOLS

(71) Applicant: Medtronic, Inc., Minneapolis, MN (US)

(72) Inventors: Kevin R. Seifert, Forest Lake, MN (US); Nathan L. Olson, Shoreview, MN (US); Rebecca L. Poindexter, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 752 days.

(21) Appl. No.: 14/193,573

(22) Filed: Feb. 28, 2014

(65) Prior Publication Data
US 2015/0133951 A1    May 14, 2015

Related U.S. Application Data

(60) Provisional application No. 61/902,847, filed on Nov. 12, 2013.

(51) Int. Cl.
*A61N 1/05*   (2006.01)
*A61B 17/34*   (2006.01)

(52) U.S. Cl.
CPC ........ *A61N 1/0504* (2013.01); *A61B 17/3415* (2013.01); *A61B 17/3468* (2013.01); *A61N 1/0563* (2013.01)

(58) Field of Classification Search
CPC ............ A61B 17/3415; A61B 17/3421; A61B 17/3417; A61B 17/3423; A61B 17/3403;
(Continued)

(56) References Cited

U.S. PATENT DOCUMENTS

| | | |
|---|---|---|
| 4,030,509 A | 6/1977 | Heilman et al. |
| 4,146,037 A | 3/1979 | Flynn et al. |
| (Continued) | | |

FOREIGN PATENT DOCUMENTS

| | | |
|---|---|---|
| CN | 2364868 Y | 2/2000 |
| CN | 101502699 A | 8/2009 |
| (Continued) | | |

OTHER PUBLICATIONS

Tung et al., "Minimal Invasive Extra Cardiac Placement of High Voltage Defibrillator Leads", Poster 3; S200 Abstract, PO-3-4; St. Paul Hospital, Vancouver, British Columbia, Canada, 1 page.
(Continued)

*Primary Examiner* — Julie A Szpira

(57) ABSTRACT

Implant tools and techniques for implantation of a medical lead, catheter or other component are provided. The implant tools and techniques are particularly useful in implanting medical electrical leads in extravascular locations, including subcutaneous locations. An implant tool for implanting a medical lead may include a shaft having a proximal end, a distal end, an open channel that extends from near the proximal end to the distal end, and an attachment feature configured to couple to the medical lead. Such an implant tool provides a user with the versatility to use the same implant tool to either pull the lead through a tunnel formed via the implant tool or push the lead through the tunnel via the open channel in the implant tool.

34 Claims, 32 Drawing Sheets

(58) Field of Classification Search
CPC ..... A61B 17/3468; A61B 2017/00477; A61M 25/0662; A61M 2025/0681
See application file for complete search history.

(56) References Cited

U.S. PATENT DOCUMENTS

| | | | |
|---|---|---|---|
| 4,270,549 A | 6/1981 | Heilman | |
| 4,280,510 A | 7/1981 | O'Neill | |
| 4,291,707 A | 9/1981 | Heilman et al. | |
| 4,424,818 A | 1/1984 | Doring et al. | |
| 4,437,475 A | 3/1984 | White | |
| 4,512,351 A | 4/1985 | Pohndort | |
| 4,538,624 A | 9/1985 | Tarjan | |
| 4,644,957 A * | 2/1987 | Ricciardelli | A61B 5/4362 600/372 |
| 4,765,341 A | 8/1988 | Mower et al. | |
| 4,832,687 A | 5/1989 | Smith, III | |
| 5,036,854 A | 8/1991 | Schollmeyer et al. | |
| 5,125,904 A | 6/1992 | Lee | |
| 5,176,135 A | 1/1993 | Fain et al. | |
| 5,255,691 A | 10/1993 | Otten | |
| 5,300,106 A | 4/1994 | Dahl et al. | |
| 5,312,355 A | 5/1994 | Lee | |
| 5,441,504 A | 8/1995 | Pohndorf et al. | |
| 5,456,699 A * | 10/1995 | Armstrong | A61N 1/05 606/108 |
| 5,509,924 A | 4/1996 | Paspa et al. | |
| 5,613,953 A | 3/1997 | Pohndorf | |
| 5,667,514 A * | 9/1997 | Heller | A61B 17/3403 604/160 |
| 5,671,736 A | 9/1997 | Pettit et al. | |
| 5,690,648 A | 11/1997 | Fogarty et al. | |
| 5,752,937 A | 5/1998 | Otten et al. | |
| 5,779,715 A | 7/1998 | Tu | |
| 5,782,841 A | 7/1998 | Ritz et al. | |
| 5,800,398 A * | 9/1998 | Hahnle | A61B 17/3417 604/164.11 |
| 5,853,391 A * | 12/1998 | Bell | A61M 25/065 604/158 |
| 5,871,528 A | 2/1999 | Camps et al. | |
| 5,944,732 A | 8/1999 | Raulerson et al. | |
| 5,951,518 A | 9/1999 | Licata et al. | |
| 6,032,079 A | 2/2000 | KenKnight et al. | |
| 6,104,957 A | 8/2000 | Alo et al. | |
| 6,122,552 A | 9/2000 | Tockman et al. | |
| 6,159,198 A | 12/2000 | Gardeski et al. | |
| 6,228,052 B1 | 5/2001 | Pohndorf | |
| 6,278,897 B1 * | 8/2001 | Rutten | A61N 1/056 607/122 |
| 6,283,948 B1 * | 9/2001 | McKernan | A61B 17/3417 604/272 |
| 6,324,414 B1 | 11/2001 | Gibbons et al. | |
| 6,415,187 B1 | 7/2002 | Kuzma et al. | |
| 6,436,068 B1 | 8/2002 | Bardy | |
| 6,445,954 B1 | 9/2002 | Olive et al. | |
| 6,544,247 B1 | 4/2003 | Gardeski et al. | |
| 6,605,094 B1 | 8/2003 | Mann | |
| 6,730,083 B2 | 5/2004 | Freigang et al. | |
| 6,733,500 B2 | 5/2004 | Kelley et al. | |
| 6,749,574 B2 | 6/2004 | O'Keefe | |
| 6,770,070 B1 | 8/2004 | Balbierz | |
| 6,772,014 B2 | 8/2004 | Coe et al. | |
| 6,836,687 B2 | 12/2004 | Kelley et al. | |
| 6,866,044 B2 | 3/2005 | Bardy et al. | |
| 6,868,291 B1 | 3/2005 | Bonner et al. | |
| 6,887,229 B1 | 5/2005 | Kurth | |
| 7,001,396 B2 | 2/2006 | Glazier et al. | |
| 7,033,326 B1 | 4/2006 | Pianca et al. | |
| 7,069,083 B2 | 6/2006 | Finch et al. | |
| 7,076,296 B2 | 7/2006 | Rissmann et al. | |
| 7,117,039 B2 | 10/2006 | Manning et al. | |
| 7,151,965 B2 | 12/2006 | Osypka | |
| 7,195,637 B2 | 3/2007 | Mika | |
| 7,218,970 B2 | 5/2007 | Ley et al. | |
| 7,229,450 B1 | 6/2007 | Chitre et al. | |
| 7,288,096 B2 | 10/2007 | Chin | |
| 7,316,667 B2 | 1/2008 | Lindstrom et al. | |
| 7,322,960 B2 | 1/2008 | Yamamoto et al. | |
| 7,369,899 B2 | 5/2008 | Malinowski et al. | |
| 7,389,134 B1 | 6/2008 | Karicherla et al. | |
| 7,450,997 B1 | 11/2008 | Pianca et al. | |
| 7,499,758 B2 | 3/2009 | Cates et al. | |
| 7,539,542 B1 | 5/2009 | Malinowski | |
| 7,627,375 B2 | 12/2009 | Bardy et al. | |
| 7,655,014 B2 | 2/2010 | Ko et al. | |
| 7,736,309 B2 | 6/2010 | Miller et al. | |
| 7,736,330 B2 | 6/2010 | Bardy | |
| 7,765,014 B2 | 7/2010 | Eversull et al. | |
| 7,837,671 B2 | 11/2010 | Eversull et al. | |
| 7,846,088 B2 | 12/2010 | Ness | |
| 7,930,040 B1 | 4/2011 | Kelsch et al. | |
| 7,983,765 B1 | 7/2011 | Doan et al. | |
| 8,057,486 B2 | 11/2011 | Hansen | |
| 8,060,207 B2 | 11/2011 | Wallace et al. | |
| 8,065,020 B2 | 11/2011 | Ley et al. | |
| 8,066,702 B2 | 11/2011 | Rittman et al. | |
| 8,090,451 B2 | 1/2012 | Tyson, Jr. | |
| 8,155,755 B2 | 4/2012 | Flynn et al. | |
| 8,157,813 B2 | 4/2012 | Ko et al. | |
| 8,260,436 B2 | 9/2012 | Gerber et al. | |
| 8,271,094 B1 | 9/2012 | Moffitt et al. | |
| 8,280,527 B2 | 10/2012 | Eckerdal et al. | |
| 8,340,779 B2 | 12/2012 | Harris et al. | |
| 8,340,781 B2 * | 12/2012 | Konishi | A61B 5/02007 29/592.1 |
| 8,355,786 B2 | 1/2013 | Malinowski | |
| 8,364,277 B2 | 1/2013 | Glukhovsky | |
| 8,386,052 B2 | 2/2013 | Harris et al. | |
| 8,409,233 B1 | 4/2013 | Chinn et al. | |
| 8,435,208 B2 | 5/2013 | Bardy | |
| 8,442,620 B2 | 5/2013 | Silipo et al. | |
| 8,447,398 B2 | 5/2013 | Bardy et al. | |
| 8,452,421 B2 | 5/2013 | Thenuwara et al. | |
| 8,454,552 B2 | 6/2013 | Bardy | |
| 8,478,424 B2 | 7/2013 | Tronnes | |
| 8,478,426 B2 | 7/2013 | Barker | |
| 8,942,820 B2 | 1/2015 | Doerr et al. | |
| 9,227,053 B2 | 1/2016 | Bonde et al. | |
| 2002/0120277 A1 | 8/2002 | Hauschild | |
| 2002/0120294 A1 | 8/2002 | Kroll | |
| 2003/0114908 A1 | 6/2003 | Flach | |
| 2003/0233115 A1 | 12/2003 | Eversull et al. | |
| 2004/0054388 A1 * | 3/2004 | Osypka | A61N 1/056 607/116 |
| 2004/0059348 A1 * | 3/2004 | Geske | A61B 17/22031 606/129 |
| 2004/0064147 A1 * | 4/2004 | Struble | A61M 25/0668 606/129 |
| 2004/0102829 A1 | 5/2004 | Bonner et al. | |
| 2004/0176781 A1 | 9/2004 | Lindstrom | |
| 2004/0210293 A1 | 10/2004 | Bardy et al. | |
| 2004/0236396 A1 | 11/2004 | Coe et al. | |
| 2005/0049663 A1 | 3/2005 | Harris et al. | |
| 2005/0119680 A1 | 6/2005 | Dykes | |
| 2005/0131505 A1 | 6/2005 | Yokoyama | |
| 2005/0288758 A1 | 12/2005 | Jones et al. | |
| 2006/0041295 A1 | 2/2006 | Okypka | |
| 2006/0116746 A1 | 6/2006 | Chin | |
| 2006/0122676 A1 * | 6/2006 | Ko | A61M 25/0668 607/116 |
| 2006/0253181 A1 * | 11/2006 | Schulman | A61N 1/0551 607/116 |
| 2006/0265047 A1 | 11/2006 | Dorn | |
| 2007/0100409 A1 | 5/2007 | Worley et al. | |
| 2007/0173900 A1 | 7/2007 | Siegel et al. | |
| 2007/0208402 A1 | 9/2007 | Helland et al. | |
| 2007/0249992 A1 | 10/2007 | Bardy | |
| 2008/0046056 A1 | 2/2008 | O'Connor | |
| 2008/0132933 A1 | 6/2008 | Gerber | |
| 2008/0132970 A1 | 6/2008 | Barolat | |
| 2008/0167650 A1 | 7/2008 | Joshi et al. | |
| 2008/0243219 A1 | 10/2008 | Malinowski et al. | |
| 2008/0269716 A1 | 10/2008 | Bonde et al. | |
| 2009/0076521 A1 | 3/2009 | Hansen | |

(56) References Cited

U.S. PATENT DOCUMENTS

| | | | |
|---|---|---|---|
| 2009/0157091 A1 | 6/2009 | Buysman | |
| 2009/0222021 A1 | 9/2009 | Chang | |
| 2009/0259283 A1 | 10/2009 | Brandt et al. | |
| 2009/0264780 A1 | 10/2009 | Schilling | |
| 2010/0016935 A1 | 1/2010 | Strandberg et al. | |
| 2010/0030227 A1* | 2/2010 | Kast | A61B 17/3468 606/129 |
| 2010/0030228 A1 | 2/2010 | Havel | |
| 2010/0056858 A1 | 3/2010 | Mokelke et al. | |
| 2010/0094252 A1 | 4/2010 | Wengreen et al. | |
| 2010/0113963 A1 | 5/2010 | Smits et al. | |
| 2010/0125194 A1 | 5/2010 | Bonner et al. | |
| 2010/0137879 A1 | 6/2010 | Ko et al. | |
| 2010/0152747 A1 | 6/2010 | Padiy et al. | |
| 2010/0217298 A1 | 8/2010 | Bardy | |
| 2010/0217301 A1 | 8/2010 | Bardy | |
| 2010/0249696 A1 | 9/2010 | Bardy | |
| 2010/0305428 A1 | 12/2010 | Bonner et al. | |
| 2010/0318098 A1 | 12/2010 | Lund et al. | |
| 2011/0009877 A1 | 1/2011 | Thenuwara et al. | |
| 2011/0009933 A1 | 1/2011 | Barker | |
| 2011/0022057 A1 | 1/2011 | Eigler et al. | |
| 2011/0224680 A1* | 9/2011 | Barker | A61B 17/3468 606/129 |
| 2011/0224681 A1 | 9/2011 | McDonald | |
| 2011/0257660 A1 | 10/2011 | Jones et al. | |
| 2012/0016377 A1 | 1/2012 | Geroy | |
| 2012/0029335 A1 | 2/2012 | Sudam et al. | |
| 2012/0078266 A1 | 3/2012 | Tyson, Jr. | |
| 2012/0089153 A1 | 4/2012 | Christopherson et al. | |
| 2012/0097174 A1 | 4/2012 | Spotnitz et al. | |
| 2012/0191106 A1 | 7/2012 | Ko et al. | |
| 2012/0209283 A1 | 8/2012 | Zhu | |
| 2012/0209285 A1 | 8/2012 | Barker et al. | |
| 2012/0290057 A1 | 11/2012 | Boling et al. | |
| 2013/0103049 A1 | 4/2013 | Bonde | |
| 2013/0158564 A1 | 6/2013 | Harris et al. | |
| 2013/0238067 A1 | 9/2013 | Baudino | |
| 2013/0296879 A1 | 11/2013 | Lazeroms et al. | |
| 2013/0317583 A1* | 11/2013 | Pianca | A61B 17/3468 607/116 |
| 2014/0012292 A1 | 1/2014 | Stewart | |
| 2014/0163655 A1 | 6/2014 | Chitre et al. | |
| 2014/0276927 A1 | 9/2014 | Barker | |
| 2014/0336581 A1* | 11/2014 | Collin | A61M 25/0668 604/164.05 |
| 2015/0105793 A1 | 4/2015 | Cole et al. | |
| 2015/0133952 A1 | 5/2015 | Siefert et al. | |
| 2015/0133953 A1 | 5/2015 | Siefert et al. | |
| 2015/0133954 A1 | 5/2015 | Siefert et al. | |

FOREIGN PATENT DOCUMENTS

| | | |
|---|---|---|
| CN | 102202726 A | 9/2011 |
| CN | 103157181 A | 6/2013 |
| EP | 0517494 A2 | 12/1992 |
| WO | 9720530 A1 | 6/1997 |
| WO | 2001023035 A1 | 4/2001 |
| WO | 2004073506 A2 | 9/2004 |
| WO | 2010045228 A2 | 4/2010 |
| WO | 2013076213 A1 | 5/2013 |

OTHER PUBLICATIONS

Molina et al, "An Epicardial Subxiphoid Implantable Defibrillator Lead: Superior Effectiveness After Failure of Stndard Implants", From the Department of Surgery, Division of Cardiovascular and Thoracic Surgery and the Department of Medicine, Cardiac Arrhymthmia Center, University of Minnesota Medical School, Minneapolis, Minnesota, Pace, vol. 27, Nov. 2004, 7 pages.
(PCT/US2014/065115) PCT Notification of Transmittal of the International Search Report and the Written Opinion of the International Searching Authority, dated Jun. 30, 2015, 14 pages.
Obadia, et al., "New Approach for Implantation of Automatic Defibrillators Using Videothoracoscopy", Journal Ann Angeiol (Paris); Sep. 1994; 43 (7) Abstract Only, 1 page.
Lemmer, "Defibrillator Patch Constriction, Letter to the Editor", The Annals of Thoracic Surgery, 1996, 1 page.
Ely et al., "Thoracoscopic Implantation of the Implantable Cardioverter Defibrillator", Minimally Invasive Techniques; (Can be found on the World-Wide Web at http://chestioumal.chestpubs.org on May 6, 2013); dated Jan. 1993; 2 pages.
Damiano, "Implantation of Cardioverter Defibrillators in the Post-Sternotomy Patient", The Annals of Thoracic Surgery, 1992; 53: pp. 978-983.
Piccione, et al., "Erosion of Extrapericardial Implantable Cardioverter Defibrillator Patch Through the Gastic Fundus with Fistulous Tract Information", Cardiology in Review; 2006; 14, e21-e23 pages.
Vyhmeister et al., "Simple Approach for Extrapericardial Placement of Defibrillator Patches via Median Sternotomy", The Annals of Thoracic Surgery; 1994; 57: 4 pages.
Harman et al., "Differences in the Pathological Changes in Dogs' Hearts After Defibrillation with Extrapericardial Paddles and Implanted Defibrillator Electrodes", Journal of Pacing and Clinical Electrophysiology, Feb. 1991; vol. 14; Part 2; 5 pages.
Obadia et al., "Thoracoscopic Approach to Implantable Cardioverter Defibrillator Patch Electrode Implantation", Pacing and Clinical Electrophysiology; Jun. 1996; vol. 19; 6 pages.
Shapira, et al., A Simplied Method for Implantation of Automatic Cardioverter Defibrillator in Patients with Previous Cardiac Surgery, Pacing and Clinical Electrophysiology, Jan. Part I, 1993, vol. 16; 6 pages.
Quigley et al., "Migration of an Automatic Implantable Cardioverter-Defibrillator Patch Causing Massive Hemothorax", Journal Texas Heart Institute, Nov. 1, 1996; vol. 23, 4 pages.
Karwande et al., Bilateral Anterior Thoracotomy for Automatic Implantable Cardioverter Defibrillator Placement in Patients with Previous Sternotomy, The Annals of Thoracic Surgery; Oct. 1992; 54(4); 3 pages.
Bielefeld et al., "Thoracoscopic Placement of Implantable Cardioverter-Defibrillator Patch Leads in Sheep", Circulation; Nov. 1993, vol. 88, No. 5, Part 2; 5 pages.
Frame et al., "Long-Term Stability of Defibrillation Thresholds with Intrapericardial Defibrillator Patches", Pacing and Clinical Electrophysiology, Jan. 1993, Part II, vol. 16, 6 pages.
Lawrie et al., "Right Mini-Thoracotomy: An Adjunct to Left Subcostal Automatic Implantable Cardioverter Defibrillator Implantation", The Annals of Thoracic Surgery; 1989; 47; 4 pages.
Mitchell et al., "Experience with an Implantable Tiered Therapy Device Incorporating Antitachycardia Pacing and Cardioverter/Defibrillator Therapy", Thoracic and Cardiovascular Surgery, Abstract Only, Mar. 1993, 1 page.
Bolling et al., "Automatic Internal Cardioverter Defibrillator: A Bridge to Heart Transplantation", Heart Lung Transplantation, Abstract Only, Jul.-Aug. 1991, 1 page.
Steinke et al., Subepicardial Infarction, Myocardial Impression, and Ventricular Penetration by Sutureless Electrode and Leads, Chest; 70: 1, Jul. 1976, 2 pages.
Avogadros Lab Supply Inc., Catalog; Scoopula with Beech Wood Handle, can be found on-line at http://www.avogadro-lab-supply.com/search.php, accessed Oct. 6, 2013, 1 page.
Medtronic, Inc. 6996SQ Subcutaneous, Unipolar Lead with Defibrillation Coil Electrode, Technicial Manual, 22 pages.
Medtronic, Inc. 6996T Tunneling Tool, Technical Manual, 12 pages.
Pebax Product Brochure, 14 pages and can be found on-line at http://www.pebax.com/export/sites/pebax/content/medias/downloads/literature/pebax-product-range-brochure.pdf, 14 pages.
Cigna et al., A New Technique for Substernal Colon Transposition with a Breast Dissector: Report of 39 Cases, Journal of Plastic, Reconstructive and Aesthetic Surgery, 2006:59, 4 pages.
Office Action from U.S. Appl. No. 14/193,634, dated May 16, 2016, 17 pp.
Response to Office Action dated May 16, 2016, from U.S. Appl. No. 14/193,634, filed Aug. 16, 2016, 21 pp.
Final Office Action from U.S. Appl. No. 14/193,634, dated Dec. 9, 2016, 14 pp.

(56) References Cited

OTHER PUBLICATIONS

Response to Office Action dated Jul. 6, 2017, from U.S. Appl. No. 14/193,634, filed Oct. 6, 2017, 14 pp.
Response to Final Office Action dated Dec. 9, 2016, from U.S. Appl. No. 14/193,634, filed Feb. 9, 2017, 16 pp.
Advisory Action from U.S. Appl. No. 14/193,634, dated Feb. 22, 2017, 3 pp.
Response to Final Office Action dated Dec. 9, 2016 and Advisory Action dated Feb. 22, 2017, from U.S. Appl. No. 14/193,634, filed Mar. 9, 2017, 14 pp.
Office Action from U.S. Appl. No. 14/193,634, dated Jul. 6, 2017, 18 pp.
Notice of Appeal from U.S. Appl. No. 14/193,634, filed May 3, 2018, 1 pp.
Pre-Appeal Brief from U.S. Appl. No. 14/193,634, filed May 3, 2018, 6 pp.
Advisory Action from U.S. Appl. No. 14/193,634, dated May 3, 2018, 3 pp.
Response to Final Office Action dated Jan. 29, 2018, from U.S. Appl. No. 14/193,634, filed Mar. 28, 2018, 8 pp.
First Office Action from counterpart Chinese Patent Application No. 201480072593.0, dated Nov. 27, 2017, 8 pp.
Final Office Action from U.S. Appl. No. 14/193,634, dated Jan. 29, 2018, 25 pp.

\* cited by examiner

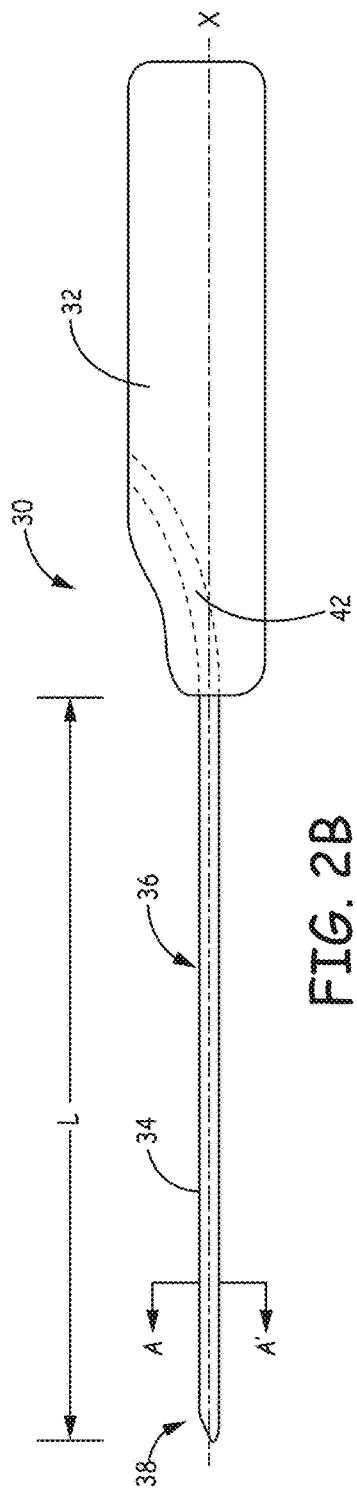
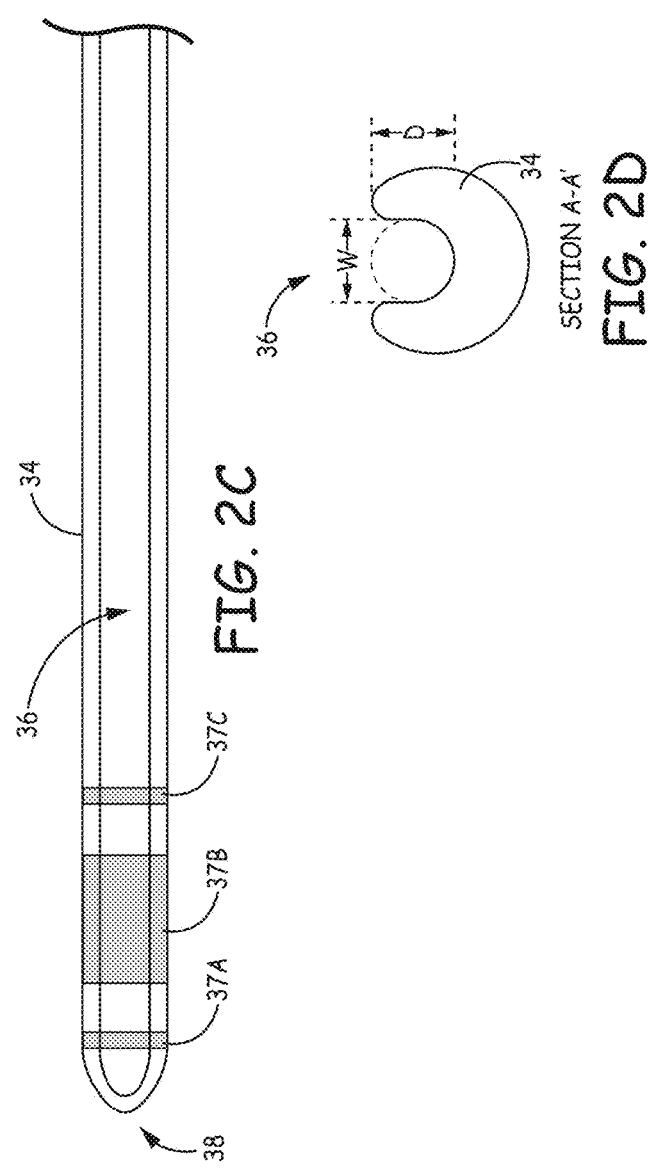
FIG. 2B
FIG. 2C
SECTION A-A'
FIG. 2D

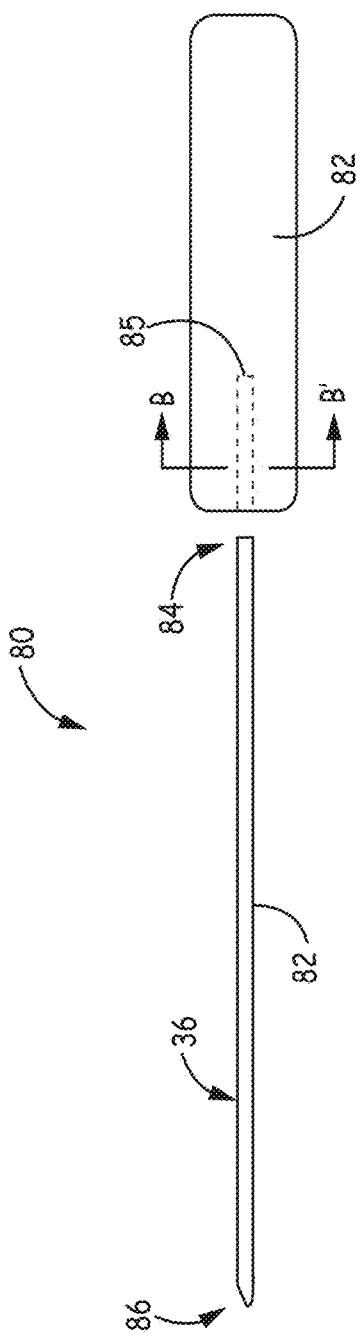
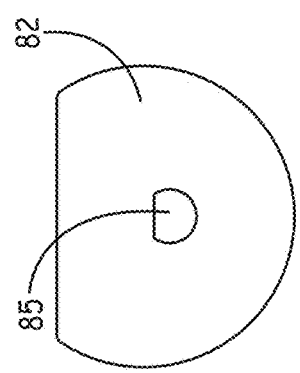

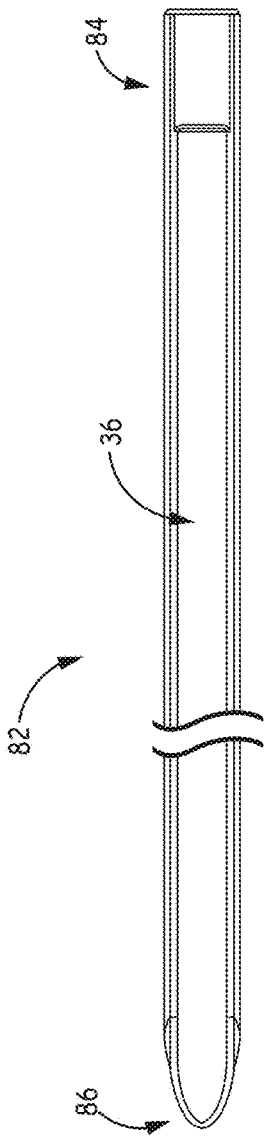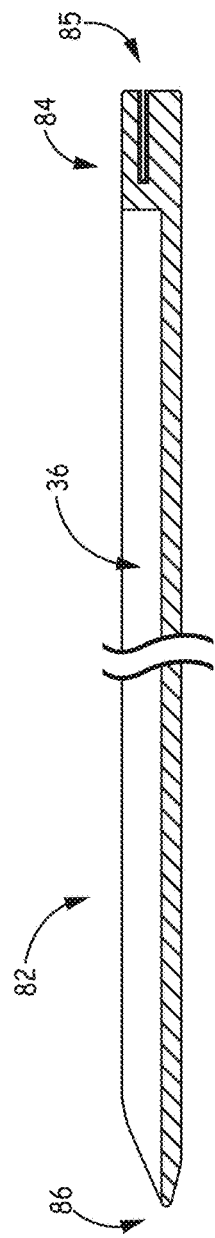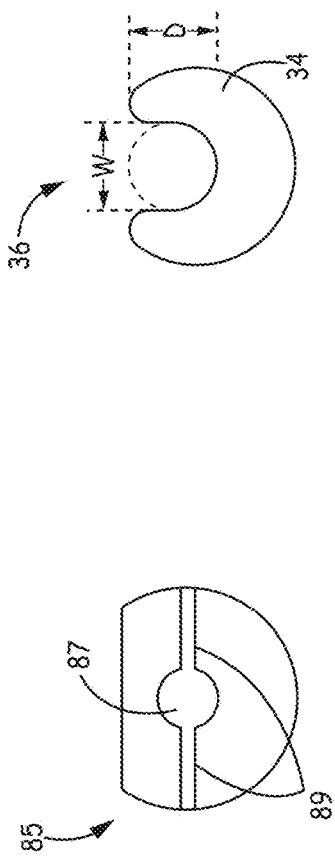

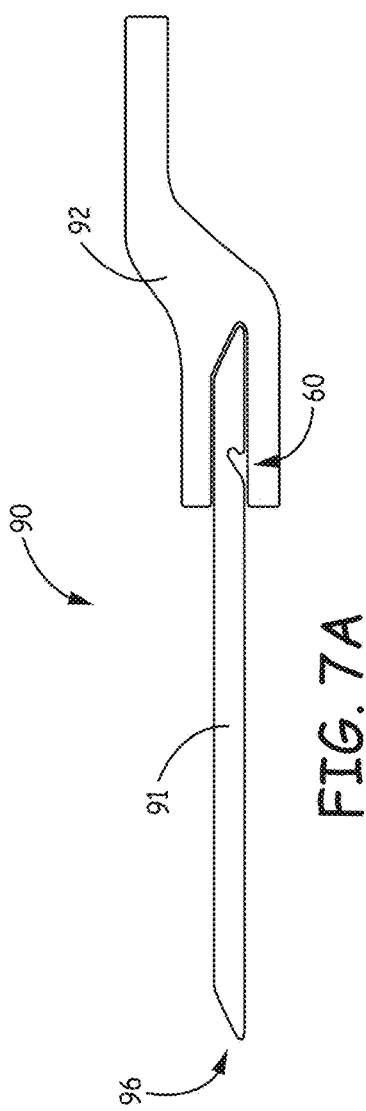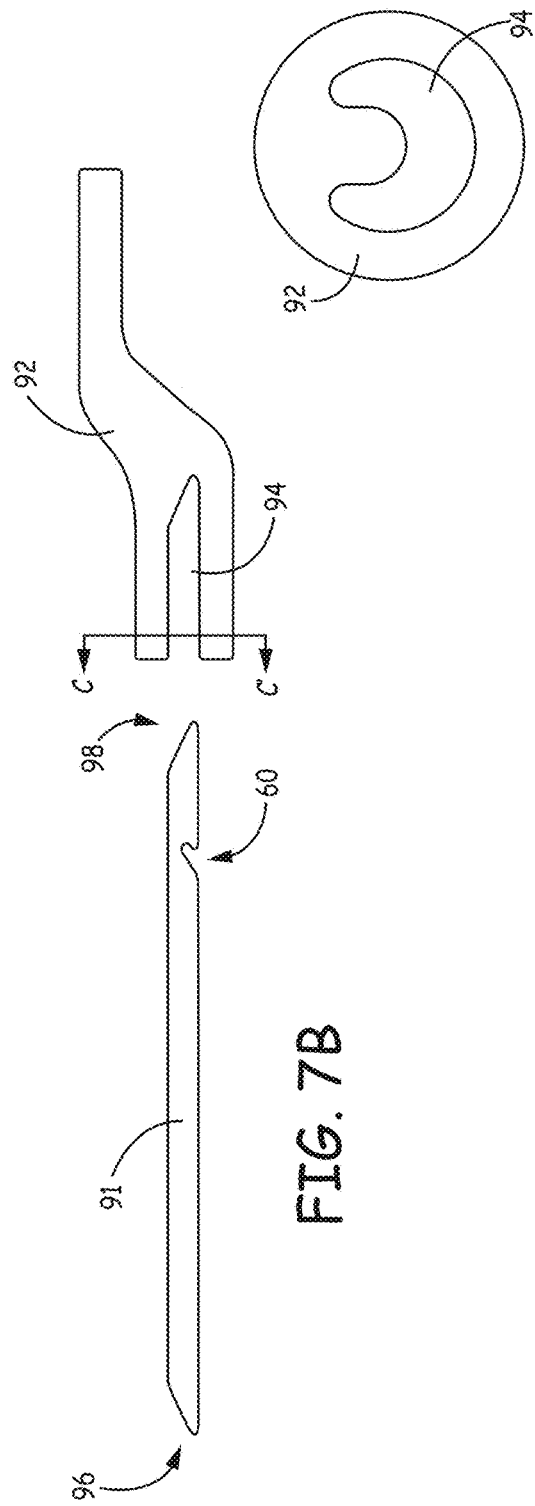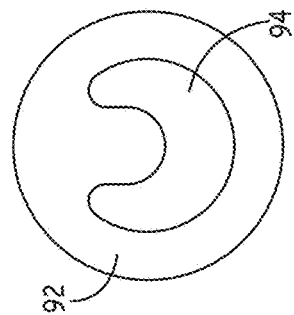

OPEN CHANNEL IMPLANT TOOLS HAVING AN ATTACHMENT FEATURE AND IMPLANT TECHNIQUES UTILIZING SUCH TOOLS

This application claims the benefit of U.S. Provisional Application No. 61/902,847, filed on Nov. 12, 2013, the content of which is incorporated herein by reference in its entirety.

TECHNICAL FIELD

The present disclosure relates to implant tools and techniques for implanting implantable medical leads or other implantable components in extravascular locations.

BACKGROUND

Implantable cardiac defibrillator (ICD) systems are used to deliver high energy electrical pulses or shocks to a patient's heart to terminate life threatening arrhythmias, such ventricular fibrillation. Traditional ICD systems include a housing that encloses a pulse generator and other electronics of the ICD and is implanted subcutaneously in the chest of the patient. The housing is connected to one or more implantable medical electrical leads that are implanted within the heart.

Traditional ICD systems that utilize transvenous leads may not be the preferable ICD system for all patients. For example, some patients with difficult vascular access precludes placement of transvenous leads. As another example, children and other younger patients may also candidates for non-transvenous ICD systems. Moreover, transvenous leads may become fibrosed in the heart over time, making lead revision and extraction procedures challenging.

A subcutaneous ICD system may be preferred for these patients. A subcutaneous ICD system includes a lead (or leads) that are implanted subcutaneously in the patient, i.e., between the skin and the ribs and/or sternum of the patient. As such, the subcutaneous ICD may eliminate the need to transvenous leads within the heart.

SUMMARY

This disclosure provides implant tools and techniques for implantation of a medical lead, catheter or other component, in extravascular locations including subcutaneous locations. In one example, this disclosure provides an implant tool for implanting a medical lead. The implant tool includes a shaft having a proximal end, a distal end, an open channel that extends from near the proximal end to the distal end, and an attachment feature configured to couple to the medical lead.

In another example, this disclosure provides a method for implanting a medical electrical lead within a patient. The method includes creating a first incision at a first location near a center of a torso of the patient, creating a second incision at a second location on a left side of the torso of the patient, introducing an implant tool into the patient via one of the first incision and the second incision, the implant tool including a handle and a shaft having a proximal end, a distal end, an open channel extending from near the proximal end to the distal end, and an attachment feature, advancing the shaft of the implant tool through the subcutaneous tissue from the incision in which the implant tool was introduced into the patient to the other one of the first incision and the second incision, attaching a lead to the attachment feature of the implant tool, and withdrawing the implant tool from the patient to pull the lead along the path created between the first incision and the second incision.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

BRIEF DESCRIPTION OF DRAWINGS

FIGS. 2A-D are conceptual drawings illustrating an example extravascular implant tool for implanting a medical lead.

FIGS. 6A-6G are schematic diagrams illustrating another implant tool for implanting a medical lead.

FIGS. 7A-7G are schematic diagrams illustrating another example implant tool for implanting a medical lead.

DETAILED DESCRIPTION

Figure 1:
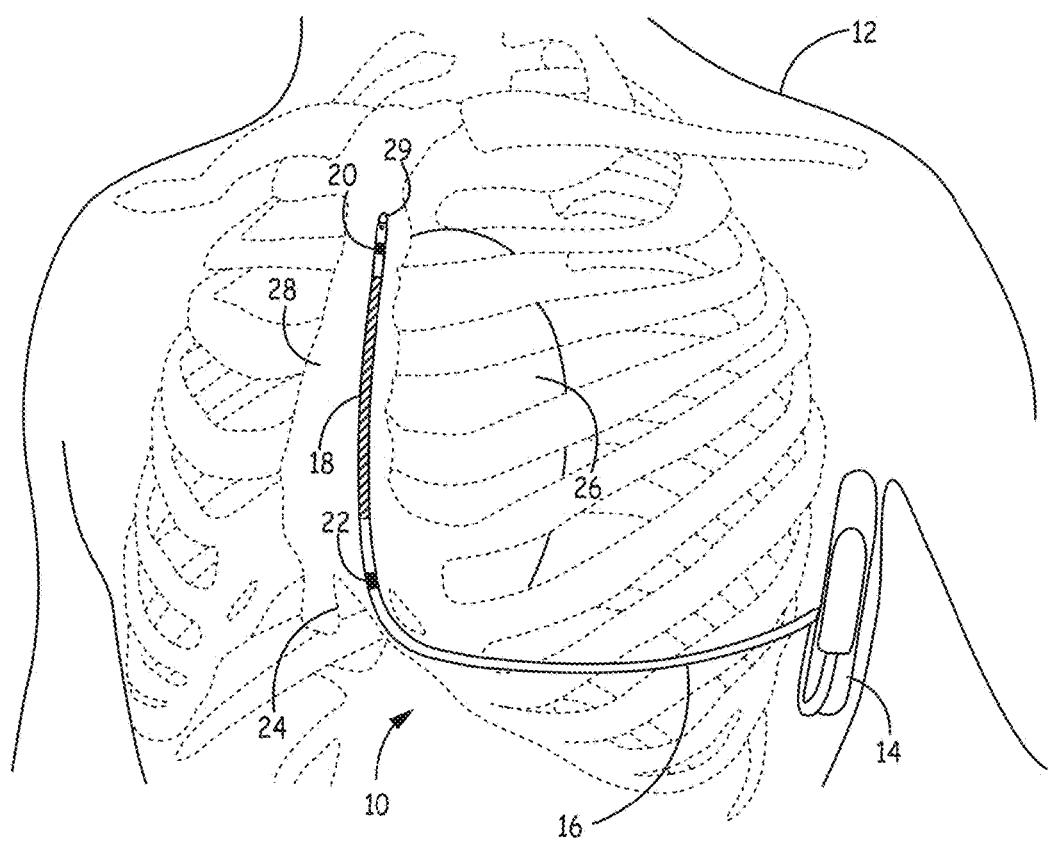
FIG. 1 is a conceptual diagram of a patient implanted with an example extravascular cardiac defibrillation system.

FIG. 1 is a conceptual diagram of a patient 12 implanted with an example extravascular cardiac defibrillation system 10. In the example illustrated in FIG. 1, extravascular cardiac defibrillation system 10 is an implanted subcutaneous defibrillation system. However, the implant tools and techniques of this disclosure may also be utilized with other extravascular implanted cardiac defibrillation systems, such as a cardiac defibrillation system having a lead implanted at least partially in a substernal or submuscular location. Additionally, the implant tools and techniques of this disclosure may also be utilized with other implantable systems, such as implantable cardioverter defibrillator systems, implantable cardiac resynchronization therapy (CRT) systems (e.g., CRT-P or CRT-D systems), implantable pacing systems, other implantable cardiac systems that include combinations of the cardiac systems above. Likewise the techniques may be used in non-cardiac implantable systems, including in implantable neurostimulation systems, drug delivery systems or other systems in which leads, catheters or other components are implanted at extravascular locations within patient 12. This disclosure, however, is described in the context of an implantable extravascular cardiac defibrillation system for purposes of illustration.

Extravascular cardiac defibrillation system 10 includes an implantable cardiac defibrillator (ICD) 14 connected to at least one implantable cardiac defibrillation lead 16. ICD 14 of FIG. 1 is implanted subcutaneously on the left side of patient 12. Defibrillation lead 16, which is connected to ICD 14, extends medially from ICD 14 toward sternum 28 and xiphoid process 24 of patient 12. At a location near xiphoid process 24 defibrillation lead 16 bends or turns and extends subcutaneously superior, substantially parallel to sternum 28. In the example illustrated in FIG. 1, defibrillation lead 16 is implanted such that lead 16 is offset laterally to the left side of the body of sternum 28 (i.e., towards the left side of patient 12).

Defibrillation lead 16 is placed along sternum 28 such that a therapy vector between defibrillation electrode 18 and a second electrode (such as a housing or can electrode of ICD 14 or an electrode placed on a second lead) is substantially across the ventricle of heart 26. The therapy vector may, in one example, be viewed as a line that extends from a point on the defibrillation electrode 18 to a point on the housing or can electrode of ICD 14. In another example, defibrillation lead 16 may be placed along sternum 28 such that a therapy vector between defibrillation electrode 18 and a housing or can electrode of ICD 14 (or other electrode) is substantially across an atrium of heart 26. In this case, extravascular ICD system 10 may be used to provide atrial therapies, such as therapies to treat atrial fibrillation.

The embodiment illustrated in FIG. 1 is an example configuration of an extravascular ICD system 10 and should not be considered limiting of the techniques described herein. For example, although illustrated as being offset laterally from the midline of sternum 28 in the example of FIG. 1, defibrillation lead 16 may be implanted such that lead 16 is offset to the right of sternum 28 or over sternum 28. Additionally, defibrillation lead 16 may be implanted such that it is not substantially parallel to sternum 28, but instead offset from sternum 28 at an angle (e.g., angled lateral from sternum 28 at either the proximal or distal end). As another example, the distal end of defibrillation lead 16 may be positioned near the second or third rib of patient 12. However, the distal end of defibrillation lead 16 may be positioned further superior or inferior depending on the location of ICD 14, location of electrodes 18, 20, and 22, or other factors.

Although ICD 14 is illustrated as being implanted near a midaxillary line of patient 12, ICD 14 may also be implanted at other subcutaneous locations on patient 12, such as further posterior on the torso toward the posterior axillary line, further anterior on the torso toward the anterior axillary line, in a pectoral region, or at other locations of patient 12. In instances in which ICD 14 is implanted pectorally, lead 16 would follow a different path, e.g., across the upper chest area and inferior along sternum 28. When the ICD 14 is implanted in the pectoral region, the extravascular ICD system may include a second lead including a defibrillation electrode that extends along the left side of the patient such that the defibrillation electrode of the second lead is located along the left side of the patient to function as an anode or cathode of the therapy vector of such an ICD system.

ICD 14 includes a housing that forms a hermetic seal that protects components within ICD 14. The housing of ICD 14 may be formed of a conductive material, such as titanium or other biocompatible conductive material or a combination of conductive and non-conductive materials. In some instances, the housing of ICD 14 functions as an electrode (sometimes referred to as a housing electrode or can electrode) that is used in combination with one of electrodes 18, 20, or 22 to deliver a therapy to heart 26 or to sense electrical activity of heart 26. ICD 14 may also include a connector assembly (sometimes referred to as a connector block or header) that includes electrical feedthroughs through which electrical connections are made between conductors within defibrillation lead 16 and electronic components included within the housing. Housing may enclose one or more components, including processors, memories, transmitters, receivers, sensors, sensing circuitry, therapy circuitry and other appropriate components (often referred to herein as modules).

Defibrillation lead 16 includes a lead body having a proximal end that includes a connector configured to connect to ICD 14 and a distal end that includes one or more electrodes 18, 20, and 22. The lead body of defibrillation lead 16 may be formed from a non-conductive material, including silicone, polyurethane, fluoropolymers, mixtures thereof, and other appropriate materials, and shaped to form one or more lumens within which the one or more conductors extend. However, the techniques are not limited to such constructions. Although defibrillation lead 16 is illustrated as including three electrodes 18, 20 and 22, defibrillation lead 16 may include more or fewer electrodes.

Defibrillation lead 16 includes one or more elongated electrical conductors (not illustrated) that extend within the lead body from the connector on the proximal end of defibrillation lead 16 to electrodes 18, 20 and 22. In other words, each of the one or more elongated electrical conductors contained within the lead body of defibrillation lead 16 may engage with respective ones of electrodes 18, 20 and 22. When the connector at the proximal end of defibrillation lead 16 is connected to ICD 14, the respective conductors may electrically couple to circuitry, such as a therapy module or a sensing module, of ICD 14 via connections in connector assembly, including associated feedthroughs. The electrical conductors transmit therapy from a therapy module within ICD 14 to one or more of electrodes 18, 20 and 22 and transmit sensed electrical signals from one or more of electrodes 18, 20 and 22 to the sensing module within ICD 14.

ICD 14 may sense electrical activity of heart 26 via one or more sensing vectors that include combinations of electrodes 20 and 22 and a housing or can electrode of ICD 14. For example, ICD 14 may obtain electrical signals sensed using a sensing vector between electrodes 20 and 22, obtain electrical signals sensed using a sensing vector between electrode 20 and the conductive housing or can electrode of ICD 14, obtain electrical signals sensed using a sensing vector between electrode 22 and the conductive housing or can electrode of ICD 14, or a combination thereof. In some instances, ICD 14 may even sense cardiac electrical signals using a sensing vector that includes defibrillation electrode 18, such as a sensing vector between defibrillation electrode 18 and one of electrodes 20 or 22, or a sensing vector between defibrillation electrode 18 and the housing or can electrode of ICD 14.

ICD may analyze the sensed electrical signals to detect tachycardia, such as ventricular tachycardia or ventricular fibrillation, and in response to detecting tachycardia may generate and deliver an electrical therapy to heart 26. For example, ICD 14 may deliver one or more defibrillation shocks via a therapy vector that includes defibrillation electrode 18 of defibrillation lead 16 and the housing/can electrode. Defibrillation electrode 18 may, for example, be an elongated coil electrode or other type of electrode. In some instances, ICD 14 may deliver one or more pacing therapies prior to or after delivery of the defibrillation shock, such as anti-tachycardia pacing (ATP) or post shock pacing. In these instances, ICD 14 may generate and deliver pacing pulses via therapy vectors that include one or both of electrodes 20 and 22 and/or the housing/can electrode. Electrodes 20 and 22 may comprise ring electrodes, hemispherical electrodes, coil electrodes, helix electrodes, segmented electrodes, directional electrodes, or other types of electrodes, or combination thereof. Electrodes 20 and 22 may be the same type of electrodes or different types of electrodes, although in the example of FIG. 1 both electrodes 20 and 22 are illustrated as ring electrodes.

Defibrillation lead 16 may also include an attachment feature 29 at or toward the distal end of lead 16. The attachment feature 29 may be a loop, link, or other attachment feature. For example, attachment feature 29 may be a loop formed by a suture. As another example, attachment feature 29 may be a loop, link, ring of metal, coated metal or a polymer. The attachment feature 29 may be formed into any of a number of shapes with uniform or varying thickness and varying dimensions. Attachment feature 29 may be integral to the lead or may be added by the user prior to implantation. Attachment feature 29 may be useful to aid in implantation of lead 16 and/or for securing lead 16 to a desired implant location. In some instances, defibrillation lead 16 may include a fixation mechanism in addition to or instead of the attachment feature. Although defibrillation lead 16 is illustrated with an attachment feature 29, in other examples lead 16 may not include an attachment feature 29. In this case, defibrillation lead 16 may be connected to or secured to an implant tool via an interference fit as will be described in more detail herein. An interference fit, sometimes also referred to as a friction fit, is a fastening between two parts which is achieved by friction after the parts are pushed together, rather than by any other means of fastening.

Lead 16 may also include a connector at the proximal end of lead 16, such as a DF4 connector, bifurcated connector (e.g., DF-1/IS-1 connector), or other type of connector. The connector at the proximal end of lead 16 may include a terminal pin that couples to a port within the connector assembly of ICD 14. In some instances, lead 16 may include an attachment feature at the proximal end of lead 16 that may be coupled to an implant tool to aid in implantation of lead 16. The attachment feature at the proximal end of the lead may separate from the connector and may be either integral to the lead or added by the user prior to implantation.

Defibrillation lead 16 may also include a suture sleeve or other fixation mechanism (not shown) located proximal to electrode 22 that is configured to fixate lead 16 near the xiphoid process or lower sternum location. The fixation mechanism (e.g., suture sleeve or other mechanism) may be integral to the lead or may be added by the user prior to implantation.

The example illustrated in FIG. 1 is exemplary in nature and should not be considered limiting of the techniques described in this disclosure. For instance, extravascular cardiac defibrillation system 10 may include more than one lead. In one example, extravascular cardiac defibrillation system 10 may include a pacing lead in addition to defibrillation lead 16.

In the example illustrated in FIG. 1, defibrillation lead 16 is implanted subcutaneously, e.g., between the skin and the ribs and/or sternum. In other instances, defibrillation lead 16 (and/or the optional pacing lead) may be implanted at other extravascular locations. In one example, defibrillation lead 16 may be implanted at least partially in a substernal location. In such a configuration, at least a portion of defibrillation lead 16 may be placed under or below the sternum in the mediastinum and, more particularly, in the anterior mediastinum. The anterior mediastinum is bounded laterally by pleurae, posteriorly by pericardium, and anteriorly by sternum. Defibrillation lead 16 may be at least partially implanted in other extra-pericardial locations, i.e., locations in the region around, but not in direct contact with, the outer surface of heart 26. These other extra-pericardial locations may include in the mediastinum but offset from sternum 28, in the superior mediastinum, in the middle mediastinum, in the posterior mediastinum, in the subxiphoid or inferior xiphoid area, near the apex of the heart, or other location not in direct contact with heart 26 and not subcutaneous. In still further instances, the implant tools described herein may be utilized to implant the lead at a pericardial or epicardial location outside the heart 26. Moreover, implant tools such as those described herein may be used to implant non-cardiac leads in other locations within patient 12.

Figure 2A:
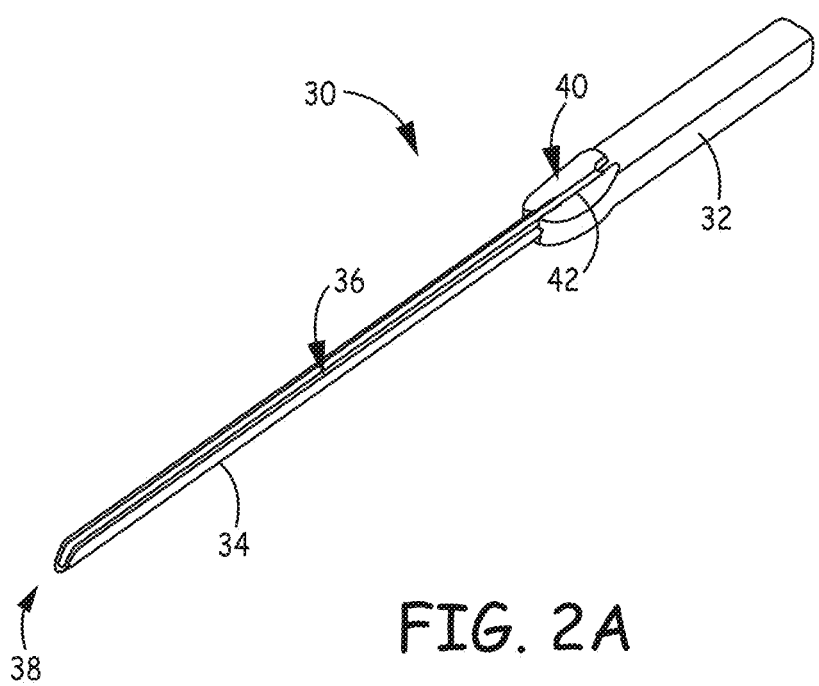

FIGS. 2A-D are conceptual drawings illustrating an example extravascular implant tool 30 for implanting a medical lead, such as lead 16 of FIG. 1, a catheter, or other implantable component. FIG. 2A illustrates an angled view of implant tool 30. FIG. 2B illustrates a longitudinal side view of implant tool 30. FIG. 2C illustrates a top view of a shaft of implant tool 30. FIG. 2D illustrates a cross sectional view of a distal end of implant tool 30 taken from A-A' in FIG. 2B. As will be described in further detail herein, implant tool 30 of FIGS. 2A-D may be particularly useful in implanting defibrillation lead 16 in patient 12 in a subcutaneous, substernal, or other extravascular location.

Implant tool 30 includes a handle 32 and an elongate shaft 34 adjacent to handle 32. Shaft 34 defines an open channel 36 that extends from handle 32 to a distal end 38. Open channel 36 may extend the entire length of shaft 34 from handle 32 to distal end 38. Shaft 24 has a length, labeled "L" in FIG. 2B. The length L of shaft 34 may be determined based on the desired tunneling application. For subcutaneous tunneling, shaft 34 may have a length between approximately 5 to 11" in some instances. However, other lengths may be appropriate for other desired applications.

Shaft 34 may have a relatively uniform thickness along the longitudinal length of shaft 34, e.g., along major axis "X" defined by implant tool 30. Alternatively, the thickness of the walls of shaft 34 may not be uniform along the length of shaft 34. For example, the walls of shaft 34 may have an increased thickness toward distal end 38 compared to the proximal end of shaft 34. The increase in thickness toward distal end 38 may enable improved tunneling performance by increasing rigidness or stiffness at distal end 38 or by reducing interference with the tissue. Additionally, the increase thickness of distal end 38 may aid in shaping distal end to avoid coring, cutting, or puncturing of tissue, pleura, pericardium or other parts of patient 12. In other instances, distal end 38 and the proximal end near handle 32 of shaft 34 may have a greater thickness compared to the middle portion of shaft 34.

In some instances, shaft 34 may include markings 37A-C (collectively, markings 37) that may aid the user during the implant procedure. For example, the markings may be placed at locations on shaft 34 that coincide with features on lead 16 when lead 16 is placed within open channel 36 such that the distal end of lead 16 is located at the distal end 38 of shaft 34. In the example, illustrated in FIG. 2C, markings 37 coincide with electrodes 18, 20 and 22 of lead 16. In other instances, markings 37 may correspond with other features of lead 16, such as fixation mechanisms (e.g., an anchor sleeve of lead 16). In instances in which the markings coincide with features of lead 16, the user may utilize the marking prior to beginning the procedure to place landmarks on the skin of patient 12. For example, prior to creating incisions, the user may place the implant tool on the skin of the patient such that the markings of the shaft coinciding with a desired location of the electrodes 18, 20 and 22 of lead 16. The user may then place landmarks on the skin of patient 12, such as landmarks corresponding with a desired end point of a tunnel or a desired tunneling path that places the features (e.g., electrodes 18, 20, and 22) of lead 16 at the desired location. In this manner, the user may use the markings on the shaft of implant tool 30 to be more confident that when insertion tool 30 is routed according to the landmarks on the skin that the electrodes or other lead features will be in the desired locations. The markings 37 may additionally or alternatively provide the user feedback regarding the distance tunneled, in which case the markings may be located toward the proximal end of shaft 34. Markings 37 may be laser etched, printed, or otherwise placed on shaft 34 of implant tool 30. Markings 37 may be made within open channel 36 and/or on the outer surface of shaft 34.

As illustrated in the cross sectional view of distal end 38 of shaft 34, taken perpendicular to the longitudinal length of shaft 34 from handle 32 to distal end 38 (e.g., orthogonal to the major axis X defined by implant tool 30), sheath 34 has a generally C-shaped cross section that defines a generally C-shaped open channel 36. In other examples, however, the cross-section of shaft 34 and open channel 36 may be formed into any of a number of different shapes including, but not limited to, a U-shape, horseshoe-shape, arc-shape, or other shape.

Open channel 36 has a depth, labeled "D" in FIG. 2D. Depth D of channel 36 may, in one example, be approximately equal to an outer diameter the lead. In some other instances, the depth D of open channel 36 may be slightly larger than the outer diameter of the lead to provide some margin. In further instances, open channel 36 may be sized to account for the largest portion of the lead, such as a fixation mechanism (such as tines), an anchoring sleeve, a connector, or other portion of the lead, with or without margin. The margin may allow the user push the lead along open channel 36 without too much interference or friction.

Open channel 36 also includes a width, labeled "W" in FIG. 2D. In one example, width W of open channel 36 is greater than an outer diameter of the lead (e.g., the diameter of the lead plus a slight margin). In another example, width W of open channel 36 is approximately equal to the outer diameter of the lead such that when the implantable electrical lead 16 is placed within open channel 36 there is a slight interference fit.

In the examples described above, implant tool 30 may be to be used to implant a particular sized lead such that a different implant tool (e.g., having a different sized open channel 36) may be selected depending on the size of the lead to be implanted, which may range from 2 French to 11 French. In further examples, a single implant tool 30 may be designed to deliver leads having a variety of different diameters. In this case, the depth D and width W of open channel 36 may be sized for delivery of the largest diameter lead for which tool 30 is designed.

Figure 9:
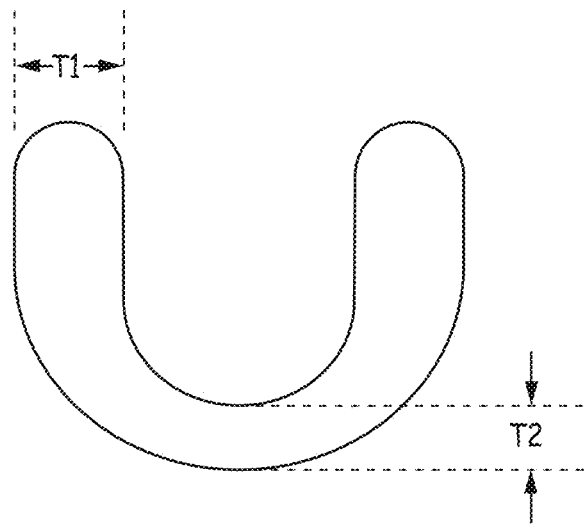
FIG. 9 illustrates a cross sectional view of an alternative shaft configuration for an implant tool.
Figure 10:
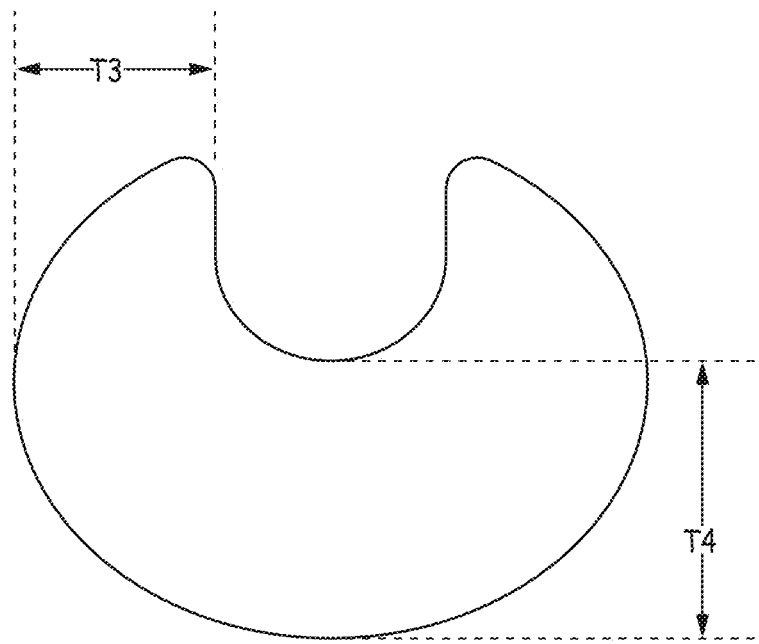
FIG. 10 illustrates a cross sectional view of another alternative shaft configuration for an implant tool.

Shaft 34 may have a relatively uniform thickness along the sides and bottom of the body of shaft 34. In other words, the walls along the sides and bottom of shaft 34 may all have about the same thickness. In another example, however, shaft 34 may have thicker walls along the sides of shaft 34 forming open channel 36 than along the bottom of shaft 34. FIGS. 9 and 10 illustrate cross sectional views of two alternative shaft configurations for an implant tool, such as implant tool 30. In the example illustrated in FIG. 9, for example, the thickness T1 along the sides of shaft 34 forming open channel 36 is greater than the thickness T2 along the bottom of shaft 34. Likewise in FIG. 10, a maximum thickness T3 along the sides of shaft 34 forming open channel 36 is less than a maximum thickness T4 along the bottom of shaft 34. Such configurations may add column stiffness and higher torsion stiffness.

Handle 32 may include a guide portion 40 near the end of handle 32 that is adjacent to shaft 34. Guide portion 40 may be used to guide defibrillation lead 16 into open channel 36. Alternatively, guide portion 40 may be used by the physician to place a portion of a lead 16 within the guide portion 40 and hold the lead in place with a finger. In the example illustrated in FIGS. 2A-C, handle 32 is tapered at the distal end and includes its own channel 42 that extends along the tapered portion of handle 32 from open channel 36. Guide portion 40 may be particularly useful in instances in which the shaft 34 is fully inserted into patient 12 via the incision thus making it difficult to access open channel 36. In other instances, handle 32 may not include a guide portion or may include a different guide portion. For example, handle 32 may have a guide portion that includes a lumen extending from the proximal end of handle 32 to open channel 36 of shaft 34. The lumen allows for passage of defibrillation lead 16 (and connector) through handle 32 and guides defibrillation lead 16 into open channel 36 of shaft 34. In some embodiments, handle 32 may include a grip portion that is offset from the portion of handle 32 adjacent to shaft 34, such as illustrated and described with respect to FIGS. 7A and 7B.

Elongate shaft 34 of implant tool 30 is formed such that it is stiff enough to be capable of being pushed through the tissue, muscle or other structure to form a path through the body. Shaft 34 may be made of a metal, polymer, or other material or combination of materials, e.g., metal and polymer. One example of a shaft having a combination of metal and polymer would be as shaft having one or more metal rods along the sides of shaft 34 or along the sides and bottom of shaft 34 and the remainder of the shaft being formed of polymer. Such a tool could be extruded, molded, or inserted as part of a manufacturing process and would provide additional stiffness and malleability to the implant tool.

In some instances, such as when shaft 34 is made of metal or a combination of metal and polymer, shaft 34 may be malleable. For example, a user of tool 30 may form shaft 34 to achieve a desired shape or bend. In this case, an implant kit may include implant tool 30 as well as bending tool (not illustrated) to aid the user in forming shaft 34 of tool 30 to the desired shape or with the desired bend. However, implant tool 30 may be shaped or bent by the user without a designated bending tool. In instances in which shaft 34 of implant tool 30 is malleable, the placement of open channel 36 and wall thickness of implant tool 30 may be altered to improve ability to be shaped with minimal deformation of open channel 36. In other instances, shaft 34 of tool 30 may not be malleable, e.g., when shaft 34 is made of a molded polymer. In further instances, the implant tool may include a pre-formed or pre-shaped shaft 34 (as will be described in more detail with respect to FIG. 17). In this case, shaft 34 may be somewhat flexible while still being stiff enough to tunnel through tissue. The flexibility may allow a user to manipulate the tool slightly to control direction (e.g., steer) of the tunnel. For example, a downward or upward force applied near the distal end of handle 32 (e.g., adjacent to shaft 34) may result in shaft 34 flexing such that distal end 38 of shaft 34 is directed upward or downward, respectively. Similarly, a force applied in to the left or right near the distal end of handle 32 may result in shaft 34 flexing such that distal end 38 of shaft 34 being directed right or left, respectively.

Handle 32 of implant tool 30 may also be made of a metal, alloy, polymer, or other material or combination of materials. Handle 32 and elongate shaft 34 may, in some instances, be constructed of the same material. For example, implant tool 30 may be formed of a single, unitary piece of material, such as metal or rigid polymer. In other instances, handle 32 and elongate shaft 34 may be constructed of different materials. In this case, handle 32 and shaft 34 may be formed of separate components that are attached together to form implant tool 30, e.g., via a two piece construction. For example, handle 32 may be made of polymer and shaft 34 may be made of metal and attached to handle 32 to form implant tool 30. Example metals or alloys from which handle 32 or shaft 34 may be constructed include, but are not limited to, stainless steel, titanium, titanium alloys, nickel-cobalt, and nickel-cobalt alloys. Example polymers may include, but are not limited to, acetal resin (e.g., DELRIN®), polyether ether ketone (PEEK), polycarbonate, polypropylene composites, and liquid-crystal polymer (LCP). In addition, lubricious fillers and coatings may be used to improve lubricity during tunneling and lead insertion. Such additives or coatings include, but are not limited to, siloxane, PTFE, and Foster ProPell™. In some instances, implant tool 30 may be a single, unitary piece of material. For example, implant tool 30 may be a rigid molded polymer tool. In other instances, handle 32 and shaft 34 may be formed of separate components that are attached together to form implant tool 30, e.g., a two piece construction. For example, handle 32 may be made of polymer and shaft 34 may be made of metal and attached to handle 32 to form implant tool 30 or both handle 32 and shaft 34 may be constructed of the same material. In some instances, handle 32 may be removable as described further with respect to FIGS. 6 and 7.

Figure 11:
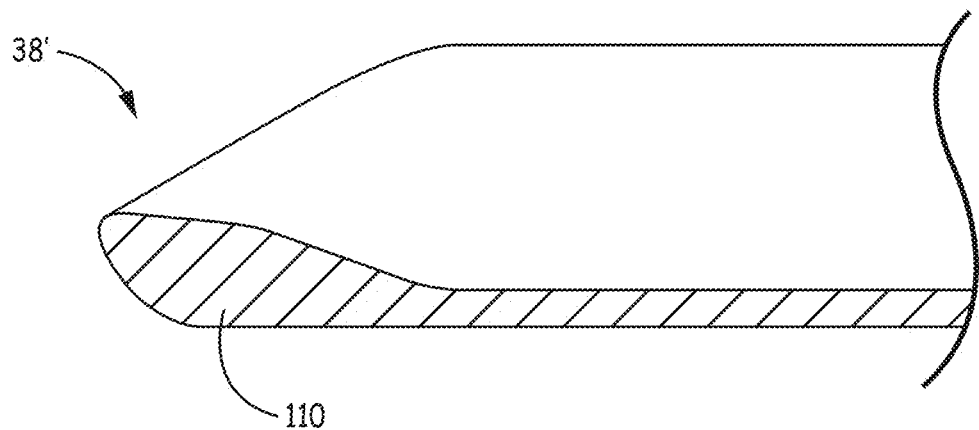
FIG. 11 illustrates a longitudinal cross-sectional view of one example alternative distal end of a shaft of an implant tool that includes a bend.
Figure 12:
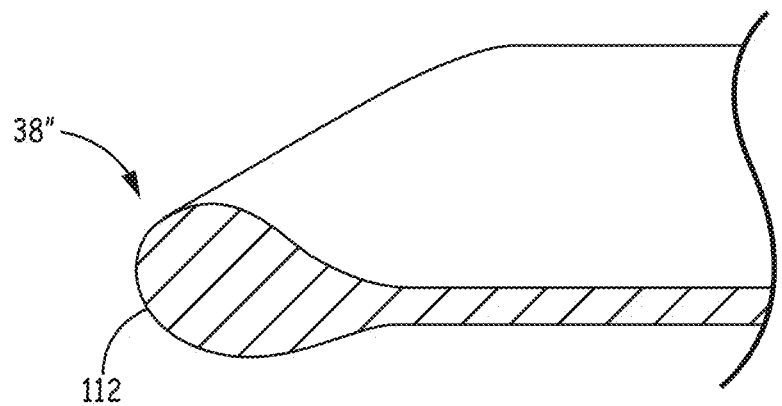
FIG. 12 illustrates a longitudinal cross-sectional view of one example alternative distal end of a shaft of an implant tool that includes a bulb-shape.

Distal end 38 of shaft 34 may be shaped to aid in tunneling through tissue or muscle. For example, distal end 38 of the shaft 34 may be tapered, angled, blunt, rounded, pointed, bent or otherwise shaped to enable a user to tunnel through subcutaneous tissue without excess damage to surrounding tissue, piercing through the skin, or coring of the tissue. FIG. 11 illustrates a longitudinal cross-sectional view of one example alternative distal end 38' of shaft 34 that includes a bend 110. FIG. 12 a longitudinal cross-sectional view of another example alternative distal end 38" of shaft 34 that include a bulb 112. Such shapes may also aid the user in tunneling, particularly through substernal locations as it may reduce the likelihood of penetration of pericardium or pleural membrane. Distal ends 38' and 38" will be described in further detail below with respect to FIGS. 11 and 12.

A user of tool 30 may insert tool 30 into an incision and tunnel distal end 38 of shaft 34 to a desired location. Once at the desired location, the user may deliver an implantable electrical lead, such as defibrillation lead 16 of FIG. 1, catheter or other implantable structure in the tunnel or path formed by implant tool 30 by pushing the defibrillation lead 16 through open channel 36 of shaft 34 and then removing tool 30 while leave defibrillation lead 16 in the path created by the implant tool.

In other instances, the implantable electrical lead 16 may be placed within open channel 36 prior to tunneling through the tissue or muscle such that the tunneling of the path and placement of lead 16 within the path occurs concurrently. Shaft 34 may also include, in some instances, a lip, hood, shield or other shape or feature that may extend partially in front of or over the distal end open channel 36. This may protect lead 16 when lead 16 is placed within open channel 36 during the tunneling procedure. Alternatively or additionally, such a feature may provide a distal end that is less likely to puncture the pleura and/or pericardium when tunneling underneath the sternum. Distal end 38' of FIG. 11 and distal end 38" of FIG. 12 illustrate two shapes of the distal end of shaft 34 that extend at least partially in front of the distal end of lead 16 when lead 16 is placed within open channel 36. Such shapes may aid in protecting the distal end of lead 16 during the tunneling of the path through the tissue, muscle or other structure of patient 12.

FIGS. 3A-H illustrate an example method of implanting a medical lead, such as defibrillation lead 16, using an implant tool, such as implant tool 30 of FIGS. 2A-C. Although FIGS. 3A-H are described in the context of utilizing implant tool 30 to implant defibrillation lead 16, other implant tools described herein may be used to implant lead 16 or any other implantable medical electrical lead, catheter or other implantable component.

Figure 3A:
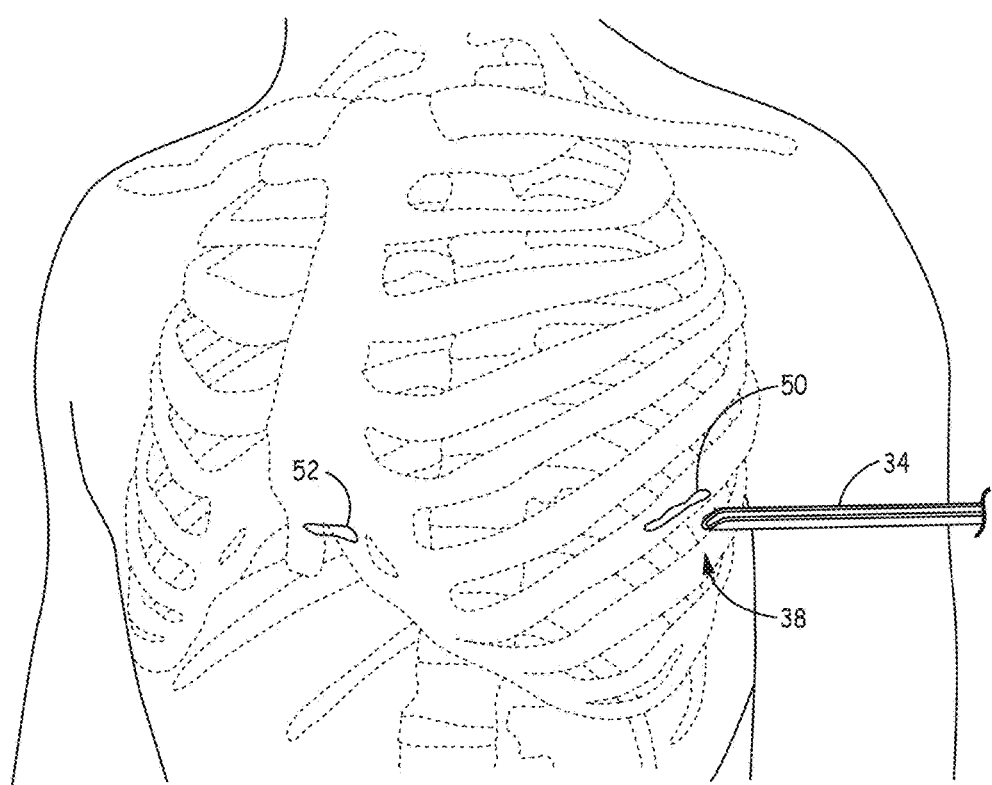
FIGS. 3A-H illustrate an example method of implanting a medical lead using implant tool of FIGS. 2A-D.

As illustrated in FIG. 3A, a first incision 50 is made at a location on the side of the torso of patient 12 and a second incision 52 is made at a location near the center of the torso of patient 12. For example, first incision 50 may be made near between the anterior axillary line and the posterior axillary line on the left side of patient 12 and second incision 52 may be made near the xiphoid process of patient 12. However, first incision 50 and second incision 52 may be made at other locations on the side and center of the torso, respectively. For example, second incision 52 may be offset to the left or right of the xiphoid process of the patient. As another example, second incision 52 may be made superior or inferior to the xiphoid process of the patient. Although described herein as first and second incisions, the incisions may be made in any order.

Figure 3B:
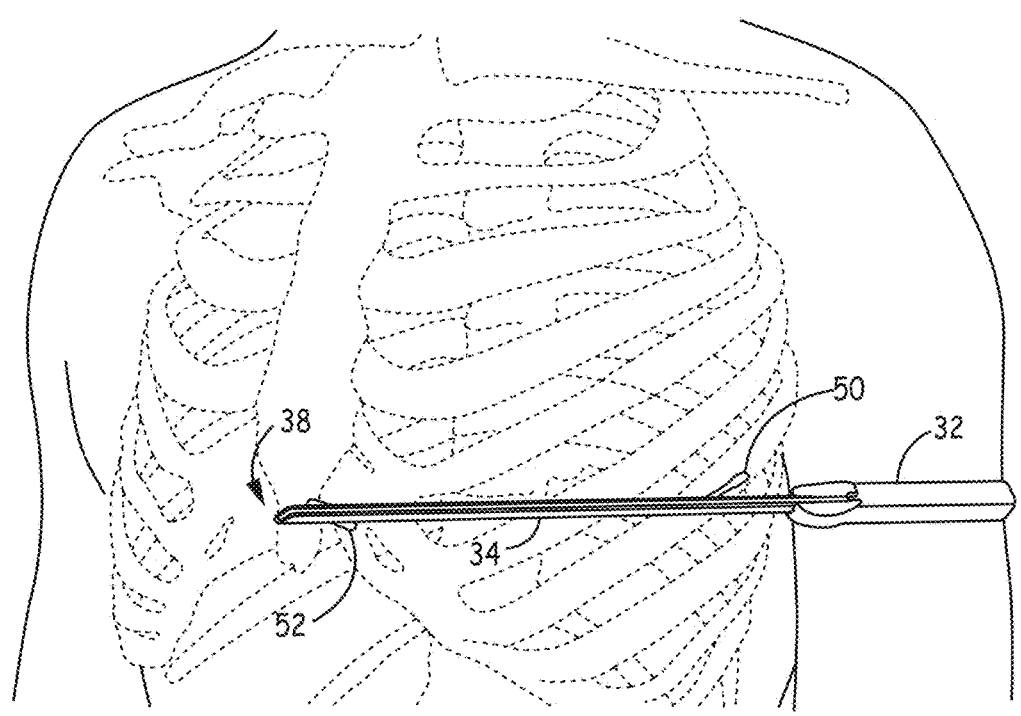

Distal end 38 of insertion tool 30 may be introduced into first incision 50 (as shown in FIG. 3A) on the left side of patient 12. Implant tool 30 is advanced through the subcutaneous tissue from first incision 50 to second incision 52 (as indicated in FIG. 3B). Implant tool 30 may be advanced until distal end 38 exits through second incision 52 or may not exit through second incision 52 but be close enough to second incision 52 such that the user may access distal end 38. As described above with respect to FIGS. 2A-D, the distal end 38 of insertion tool 30 may be shaped to aid in tunneling through subcutaneous tissue from first incision 50 to second incision 52. For example, distal end 38 of the shaft 34 may be tapered, angled, blunt, rounded, or otherwise shaped to enable a user to tunnel through subcutaneous tissue without damaging surround tissue or puncturing through the skin of patient 12.

Figure 3C:
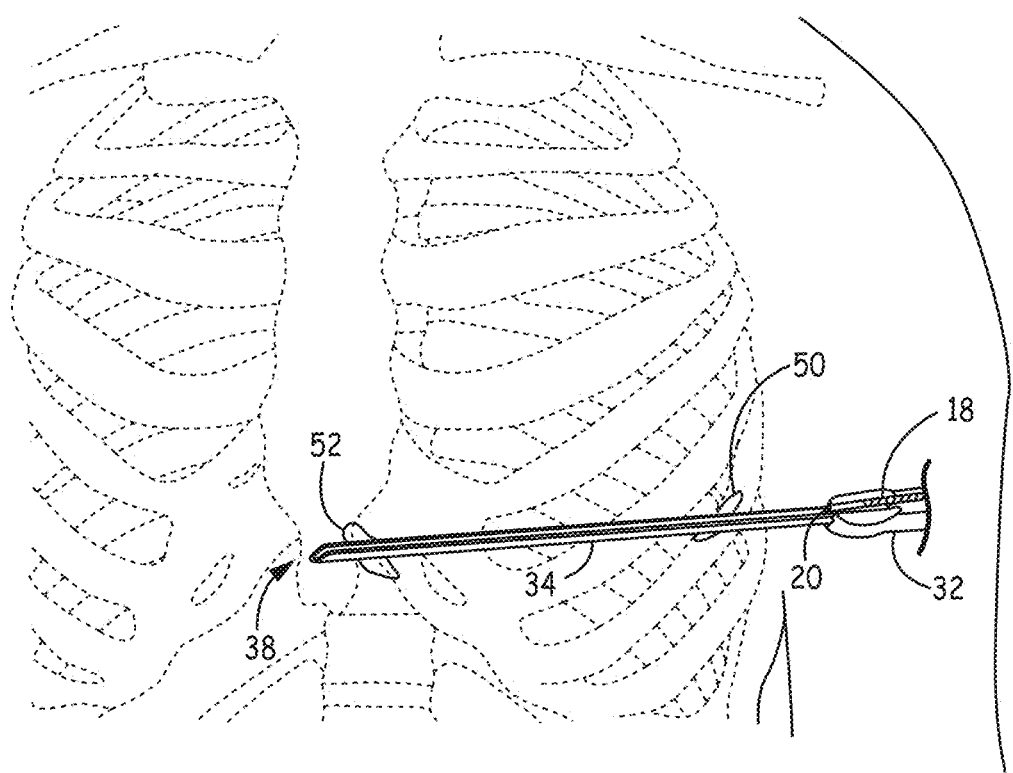
Figure 3D:
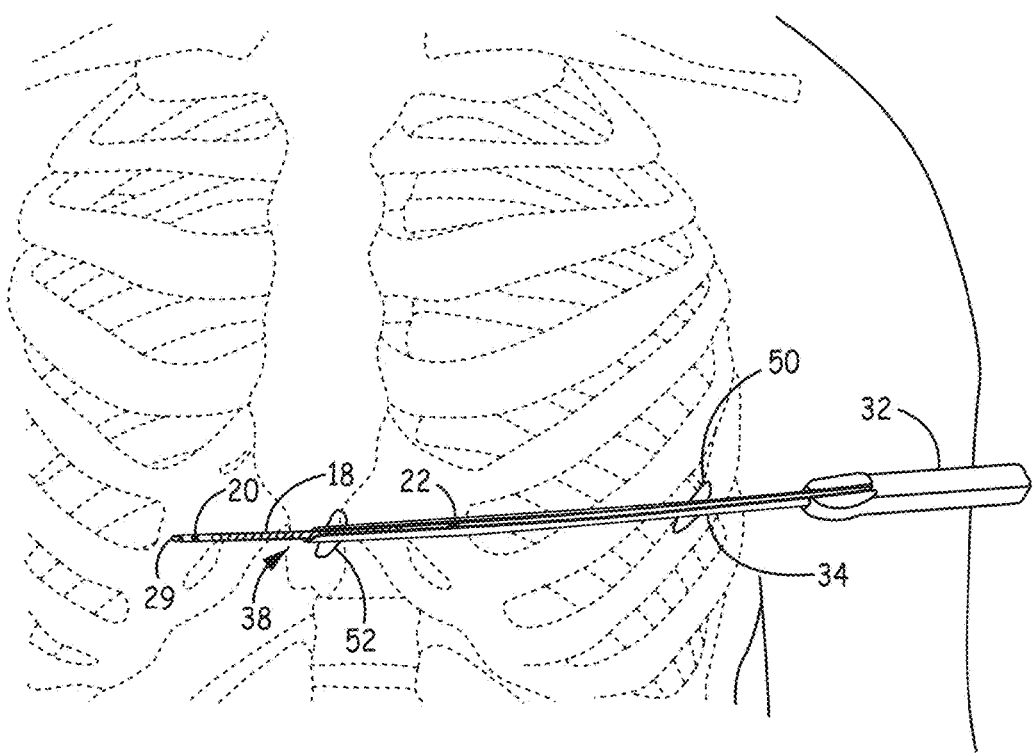
Figure 3E:
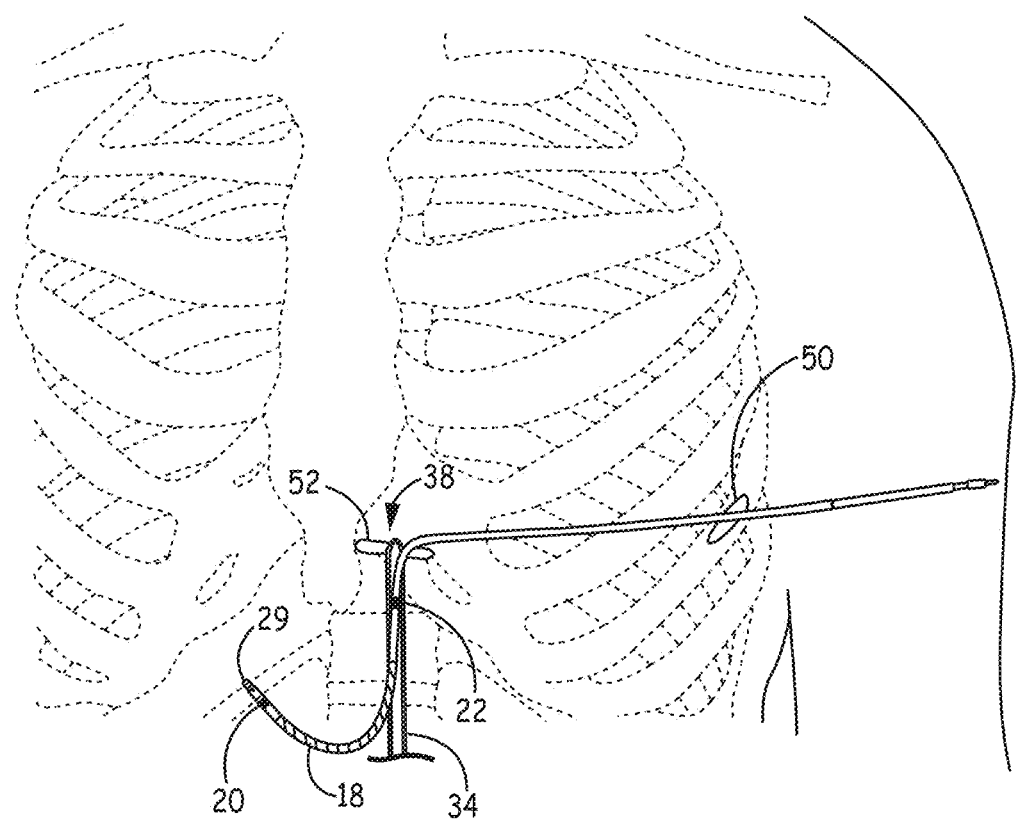

The distal end of lead 16 is introduced into open channel 36 of shaft 34 near first incision 50 (as illustrated in FIG. 3C). In one example, the distal end of lead 16 may be introduced into open channel 36 via guide portion 40 of handle 32. In other instances, the distal end of lead 16 may be introduced directly into open channel 36. Defibrillation lead 16 is advanced within open channel 36 from first incision 50 toward second incision 52 until the distal end of defibrillation lead 16 exits second incision 52 (as illustrated in FIG. 3D). Implant tool 30 is withdrawn toward first incision 50 and removed from the body of patient 12 while leaving defibrillation lead 16 in place along the path from first incision 50 to second incision 52 (as illustrated in FIG. 3E). In other words, after implant tool 30 is removed, the distal end of lead 16 is extending out of second incision 52, the proximal end of lead 16 is extending out of first incision 50 and the remainder of lead 16 is subcutaneously located in the path or tunnel formed by implant tool 30.

The steps illustrated in FIG. 3A-3C are for illustrative purposes only and should not be considered limiting of the techniques described herein. The user may place defibrillation lead 16 along the path from first incision 50 to second incision 52 in other manners. For example, implant tool 30 may be advanced through the subcutaneous tissue from second incision 52 to first incision 50 (as indicated in FIG. 3B above). In this case, the distal end of lead 16 may be introduced into open channel 36 of shaft 34 via the distal end 38 of shaft 34 near first incision 50 and advanced toward handle 32 of tool 30 located near second incision 52. Alternatively, the proximal end of lead 16 (e.g., connector) may be placed within open channel 36 of shaft 34 and advanced toward first incision 50.

Figure 3F:
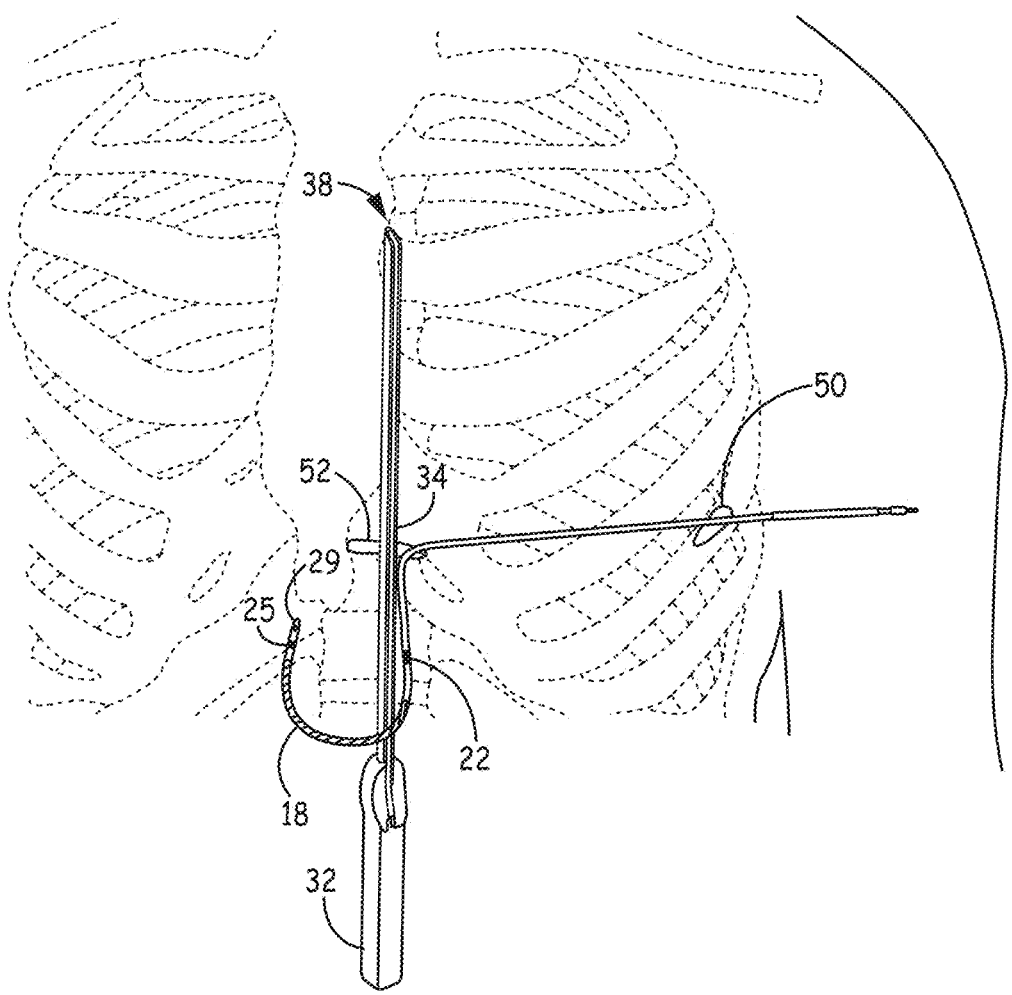

Implant tool 30 is then introduced into second incision 52 near the center of the torso of patient 12 (as illustrated in FIG. 3E). Implant tool 30 is advanced subcutaneously superior from second incision 52 substantially parallel to sternum 28 (as illustrated in FIG. 3F). In the example illustrated in FIG. 3F, the path followed by implant tool 30 is offset laterally to the left of the body of sternum 28 and distal end 38 of implant tool 30 is positioned near the second rib of patient 12. Such a path enables defibrillation lead 16 to be implanted such that the defibrillation energy delivered via electrode 18 returns to the housing electrode of ICD 14 in a vector that captures the ventricle of heart 26.

However, implant tool 30 may be advanced along other paths. For example, implant tool 30 may be advanced to create a tunnel or path that is offset from sternum 28 at an angle (e.g., angled lateral from sternum 28 at either the proximal or distal end), is offset from sternum 28 on the right side of sternum 28, over sternum 28 or other path depending on the anatomy of patient 12 and/or location of ICD 14. As another example, distal end 38 of implant tool 30 may be positioned further superior or inferior depending on the location of ICD 14 relative to lead 16, placement of electrodes 18, 20 and 22 on lead 16, and other factors.

In other examples, implant tool 30 may be introduced into second incision 52 and advanced to create a tunnel or path that is not subcutaneous, but instead is substernal. For example, implant tool 30 may be advanced under or below the sternum. Description of other locations are provided above with respect to FIG. 1.

Figure 3G:
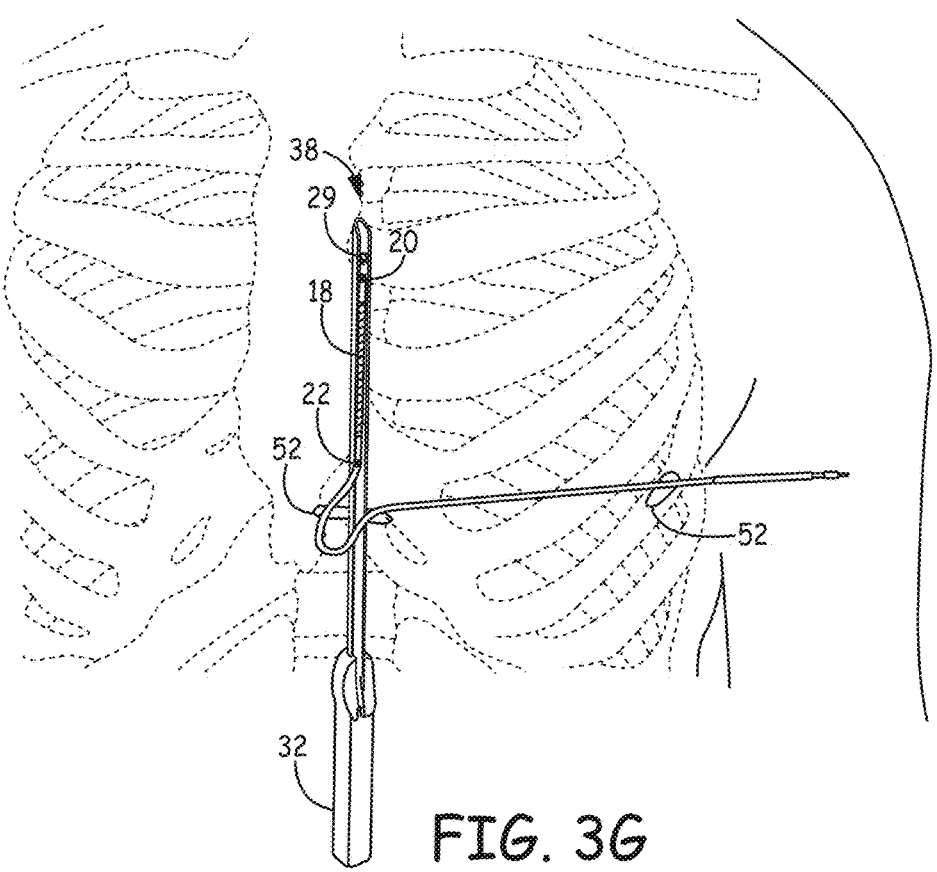

The distal end of lead 16 is introduced into open channel 36 of shaft 34 near second incision 52. In one example, the distal end of lead 16 may be introduced into open channel 36 via guide portion 40 of handle 32. The distal end of defibrillation lead 16 is advanced along open channel 36 from second incision 52 toward distal end 38 of shaft 34 (as illustrated in FIG. 3G). Defibrillation lead 16 may encounter resistance upon reaching distal end 38 of shaft 34 as there is no subcutaneous path past distal end 38 of shaft 34.

Figure 3H:
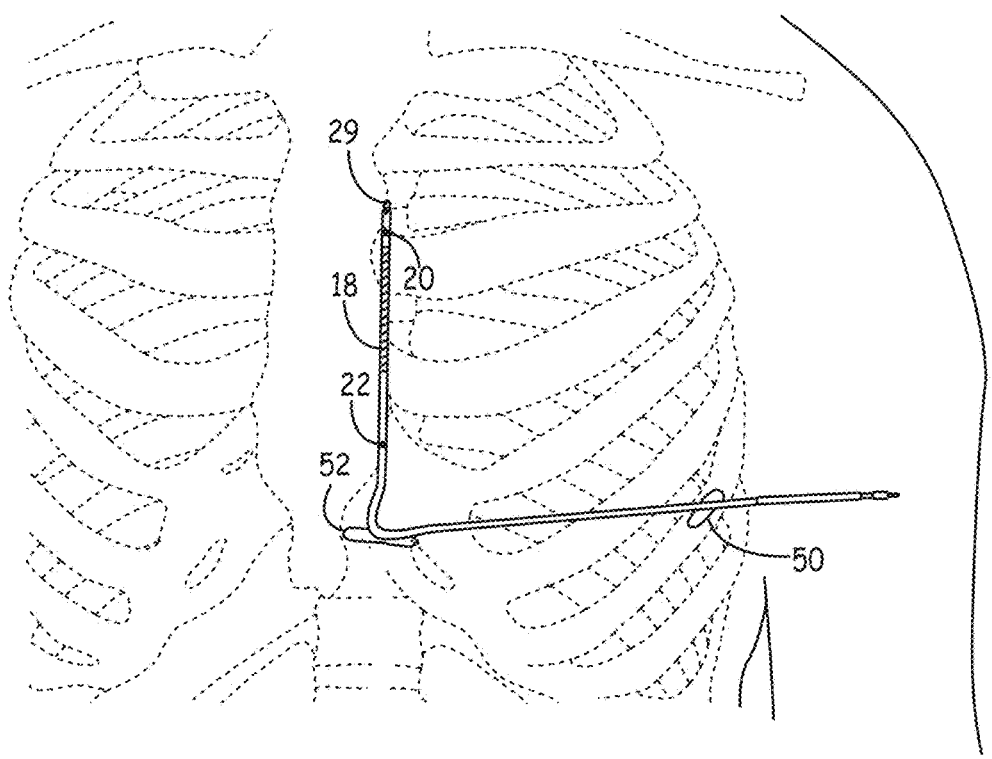

Implant tool 30 is withdrawn toward second incision 52 and removed from the body of patient 12 while leaving defibrillation lead 16 in place along the path from the second incision to the superior location (as illustrated in FIG. 3H). In some instances, the distal end of lead 16 may include an anchoring mechanism to fixate the distal end of lead 16 in place near the superior location (e.g., near the second or third rib). The anchoring mechanism may include tines, a helix, or other anchoring mechanisms. In other examples, a third incision may be made near the superior location, e.g., toward the top of sternum 28 proximate the desired location of the distal end of defibrillation lead 16. In this case, implant tool 30 may be advanced subcutaneously from second incision 52 to the third incision until distal end 38 is proximate to and possibly exits the third incision. The distal end of defibrillation lead 16 would also be advanced through open channel 36 until it is adjacent to the third incision. The distal end of defibrillation lead 16 may then be affixed to the desired location proximate the third incision via a fixation mechanism separate from defibrillation lead 16, e.g., sutures, staples, anchor sleeve, or the like, or built into defibrillation lead 16, e.g., tines, helix or other built in fixation mechanism.

The portion of defibrillation lead 16 proximate second incision 52 may also be affixed to the desired location proximate second incision 52 via a fixation mechanism separate from defibrillation lead 16, e.g., sutures, staples, anchor sleeve, or the like, or built into defibrillation lead 16, e.g., tines, helix or other built in fixation mechanism.

A subcutaneous pocket may be created near first incision 50 and ICD 14 may be placed within the subcutaneous pocket. A connector of defibrillation lead 16 is mechanically coupled to the connector block of ICD 14. The various incision and pockets may then be closed to complete the implant procedure.

The example method of implanting a lead illustrated in FIGS. 3A-H is exemplary in nature and should not be considered limiting of the techniques described in this disclosure. Other techniques may be utilized using implant tool 30. For example, lead 16 may first be implanted along sternum 28 as described in FIGS. 3F-H and then tunneled over to the left side of patient 12, e.g., from incision 52 to incision 50. As another example, instead of advancing implant tool 30 and then pushing lead 16 through open channel 36, lead 16 may be placed within open channel of implant tool 30 prior to introducing lead inserting tool 30 into the incisions such that both the implant tool 30 and lead 16 are tunneled through the tissue at the same time. In a further example, ICD 14 may be placed in the upper right pectoral region and lead 16 may be implanted across the chest and then turn and follow a path inferior along sternum 28.

In still other examples, a third incision may be made superior to incision 52. Implant tool 30 may be used to tunnel a path from incision 52 to the third incision or from third incision to incision 52. The proximal or distal end of the lead may then be advanced through open channel 36 either from incision 52 to the third incision or from the third incision to incision 52 to place the lead within the path formed via tunneling.

Also, as described above with respect to FIG. 2, prior to creating incisions, the user may place the implant tool on the skin of the patient such that the markings of the shaft coinciding with a desired location of the electrodes 18, 20 and 22 of lead 16. The user may then place landmarks on the skin of patient 12, such as landmarks corresponding with a desired end point of a tunnel or a desired tunneling path that places the features (e.g., electrodes 18, 20, and 22) of lead 16 at the desired location. In this manner, the user may use the markings on the shaft of implant tool 30 to be more confident that when insertion tool 30 is routed according to the landmarks on the skin that the electrodes or other lead features will be in the desired locations.

Figure 4A:
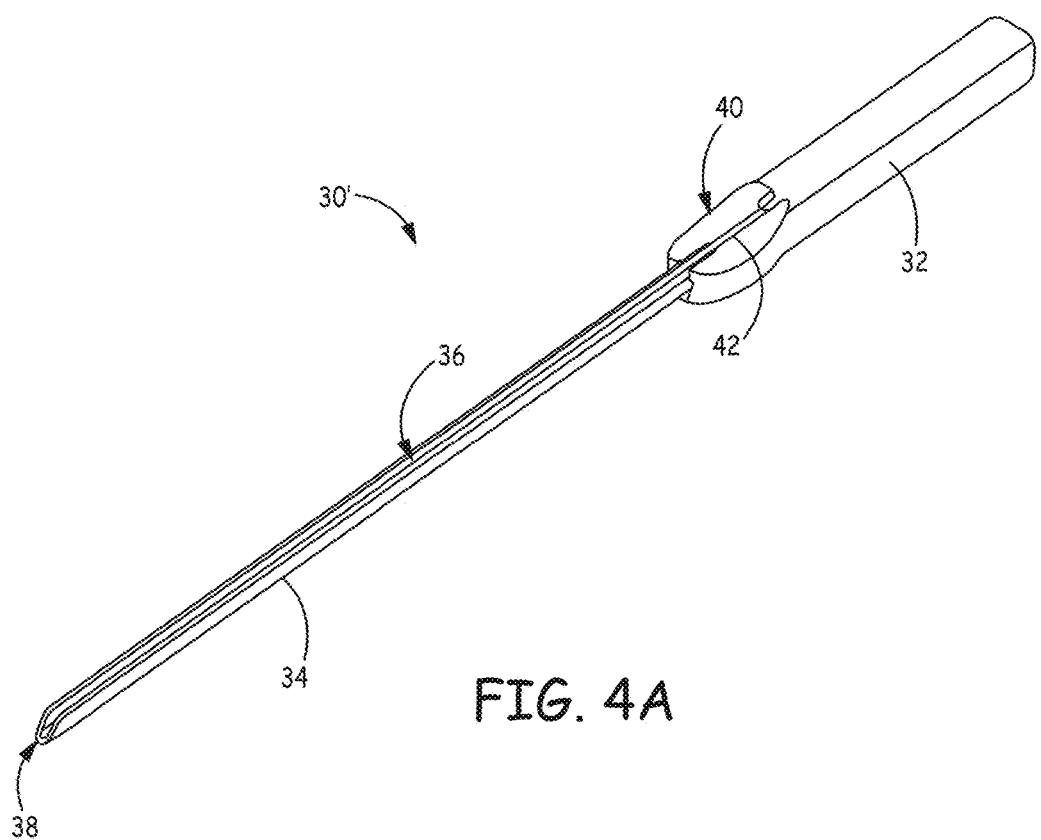
FIGS. 4A-D are conceptual drawings illustrating another example implant tool for implanting a medical lead.
Figure 4B:
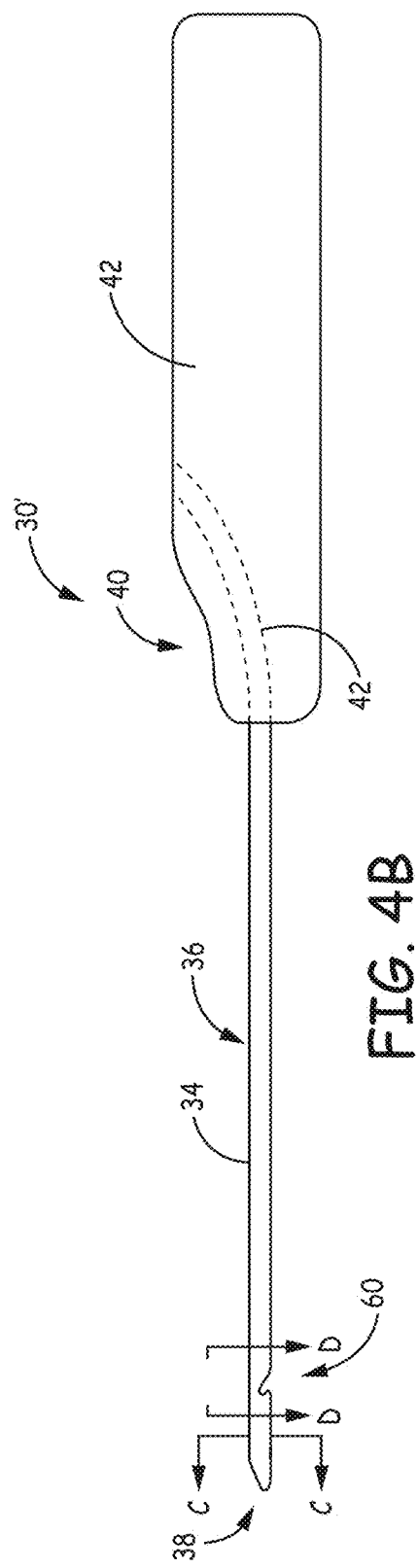
Figure 4D:
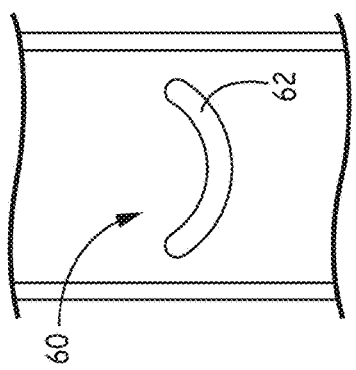
Figure 4C:
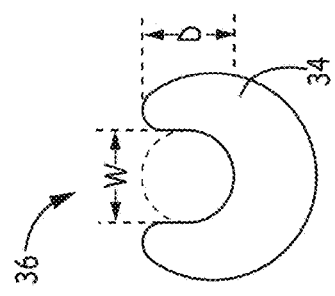

FIGS. 4A-D are conceptual drawings illustrating another example implant tool 30'. FIG. 4A illustrates an angled view of implant tool 30'. FIG. 4B illustrates a longitudinal side view of implant tool 30'. FIG. 4C illustrates a cross sectional view of a distal end of implant tool 30' taken from C-C' in FIG. 4B. FIG. 4D illustrates a cross sectional view of a hook feature taken from D-D' in FIG. 4B.

Implant tool 30' can include one or more of the structure and/or functionality of implant tool 30 of FIGS. 2A-D (and vice versa). Repetitive description of like numbered elements described in other embodiments is omitted for sake of brevity. Implant tool 30' conforms substantially with implant tool 30 of FIGS. 2A-D except implant tool 30' includes a hook feature 60 toward distal end 38 of tool 30' to couple to an attachment feature of implantable medical lead 16, such as attachment feature 29 illustrated in FIG. 1.

Hook feature 60 is a mechanism by which implant tool 30' may be attached to a medical electrical lead. As illustrated in FIG. 4B, hook feature 60 define an angled groove that extends into the outer surface of shaft 34 and toward distal end 38 of shaft 34. In one example, hook feature 60 may be formed by an angled slot on the outer, bottom portion of shaft 34. The edges of hook feature 60 may be designed to be rounded, tapered, or otherwise shaped to avoid catching on tissue or muscle when implant tool 30' is advanced or removed from body of patient 12. Hook feature 60 may be designed based on the type of attachment feature 29 of lead 16 expected to be implanted using implant tool 30'. Hook feature 60 is designed such that when implant tool 30' is being pulled, attachment feature 29 of lead 16 is preferentially pulled into the groove of hook feature 60.

In the example illustrated in FIG. 4D, the groove forming hook feature 60 extends into open channel 34, as illustrated by arc-shaped opening 62 along the bottom of open channel 36. However, hook feature 60 may be formed in a number of other shapes. In other examples, hook feature 60 may not extend through the thickness of shaft 34 into open channel 34. Instead, hook feature 60 may be an angled radial contoured cut or groove that is deep enough to catch or accept a portion of lead 26 (such as attachment feature 29), but does not extend all the way into open channel 36. In some instances, the portion of shaft 34 at which hook feature 60 is located may have an increased thickness relative to other portions of shaft 34 to enable hook feature 60 to be formed without extending all the way through into open channel 36.

Hook feature 60 may be designed such that when attachment feature 29 of lead 16 is placed within hook feature 60 a portion of attachment feature 29 fills opening 62 and/or extends over tab 64 to reduce the likelihood of catching on tissue or muscle when implant tool 30' is pulled back through the path formed in the tissue.

As will be described in further detail with respect to FIGS. 5A-H, hook feature 60 may be attached to a lead such that the lead may be pulled through a subcutaneous path as insertion tool 30' is withdrawn from the body of patient 12. For example attachment feature 29 of lead 16, which may be a suture as described above, is placed within hook feature 60, such that the lead may be pulled through a subcutaneous path as insertion tool 30' is withdrawn from the body of patient 12. In this manner, implant tool 30' may be used to either push a lead through the path in the subcutaneous tissue (as described above with respect to FIGS. 3A-H) or pull the lead through the path in the subcutaneous tissue (as described below with respect to FIGS. 5A-D). Implant tool 30' would thus provide a single tool that may be used to perform lead insertion via either technique described above.

Figure 5A:
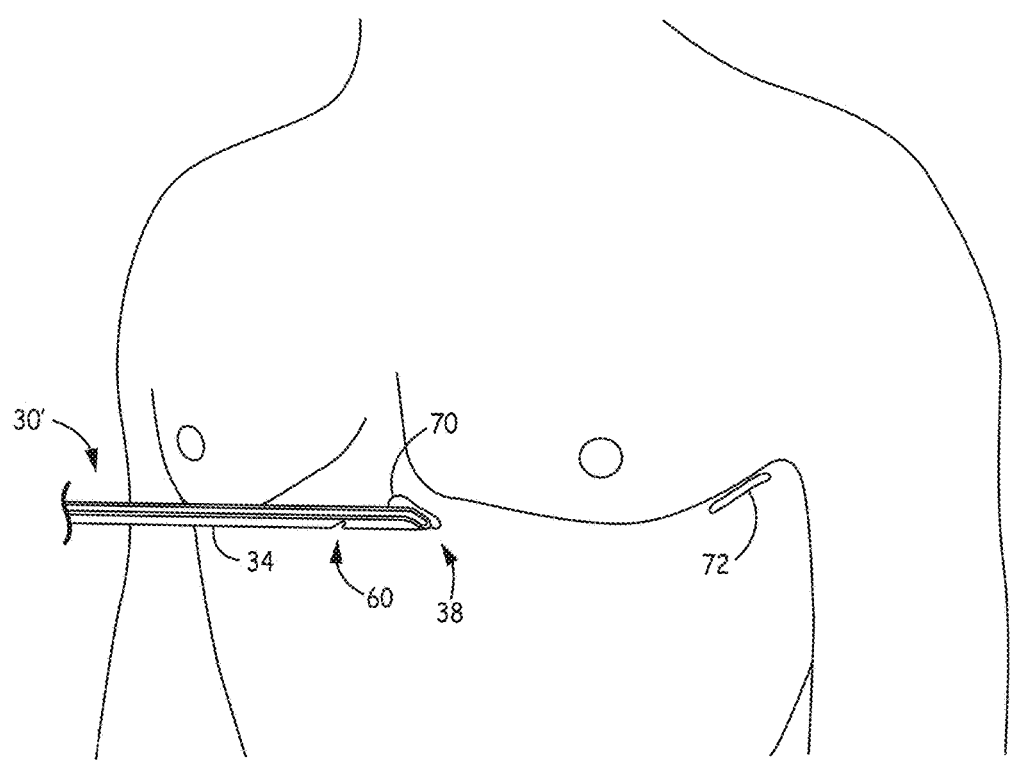
FIGS. 5A-H illustrate an example method of implanting a medical lead using the implant tool of FIGS. 4A-D.

FIGS. 5A-H illustrate an example method of implanting a subcutaneous lead, such as defibrillation lead 16, using an implant tool, such as implant tool 30' of FIGS. 4A-D. As illustrated in FIG. 5A, a first incision 70 is made at a location near the center of the torso of patient 12 and a second incision 72 is made at a location on the side of the torso of patient 12. Although described herein as first and second incisions, the incisions may be made in any order. For example, first incision 70 may be made near the xiphoid process of patient 12 and second incision 72 may be made near between the anterior axillary line and the posterior axillary line on the left side of patient 12. However, first incision 70 and second incision 72 may be made at other locations on the center and side of the torso, respectively. In some instances, prior to making incisions 70 and 72, Also, as described above with respect to FIG. 2, prior to creating incisions, the user may place the implant tool on the skin of the patient such that the markings of the shaft coinciding with a desired location of the electrodes 18, 20 and 22 of lead 16 and place landmarks on the skin of patient 12 corresponding with a desired end point of a tunnel or a desired tunneling path that places the features (e.g., electrodes 18, 20, and 22) of lead 16 at the desired location.

Figure 5B:
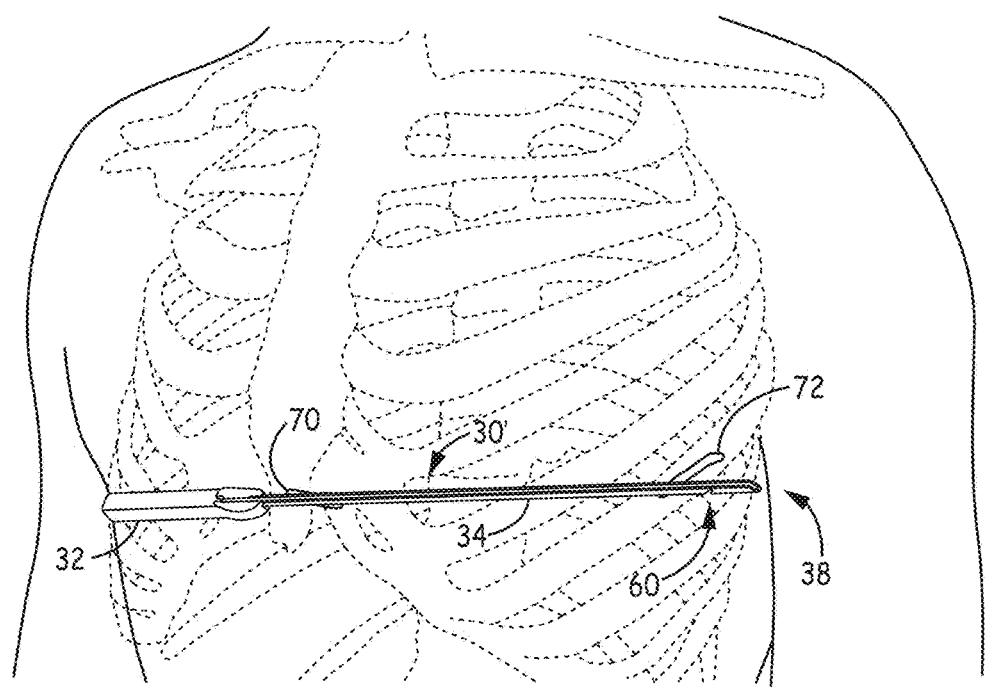

Distal end 38 of insertion tool 30' may be introduced into first incision 70 (as shown in FIG. 3A) near the center of the torso of patient 12. Implant tool 30' is advanced through the subcutaneous tissue from first incision 70 to second incision 72 until distal end 38 including hook feature 60 is proximate to and possibly exits from second incision 72 (as indicated in FIG. 5B). The distal end 38 of insertion tool 30' may be shaped to aid in tunneling through subcutaneous tissue from first incision 70 to second incision 72. For example, distal end 38 of the shaft 34 may be tapered, angled, blunt, rounded, or otherwise shaped to enable a user to tunnel through subcutaneous tissue without damaging surround tissue or puncturing through the skin of patient 12.

Figure 5C:
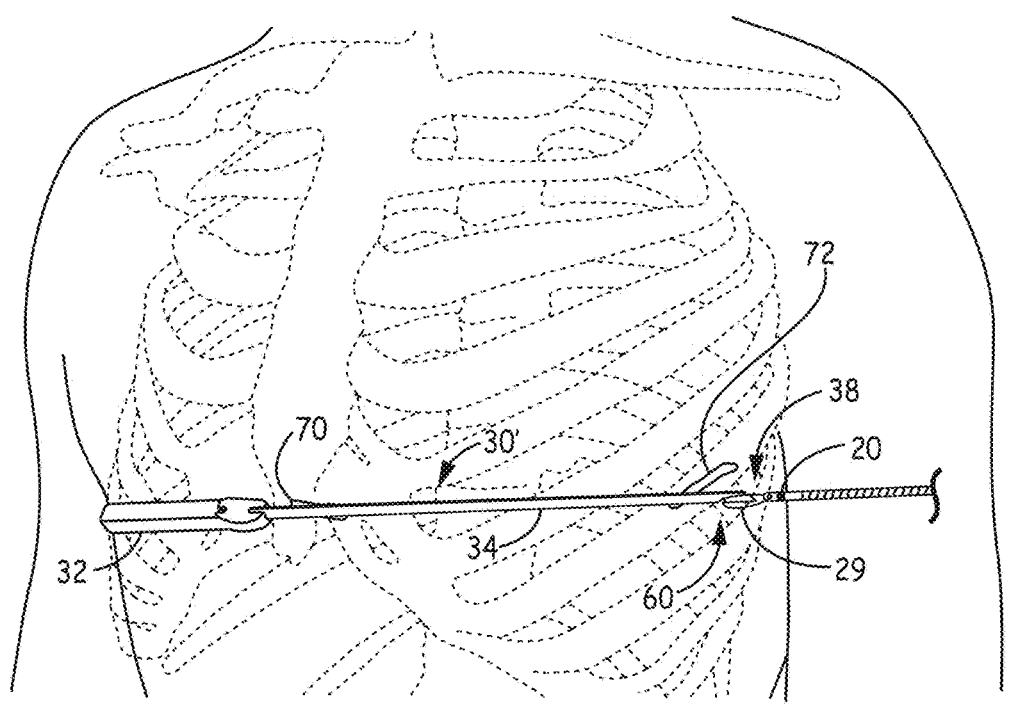

Attachment feature 29 of lead 16 is placed within hook feature 60 (as illustrated in FIG. 5C). In some instances, the distal end of lead 16 may partially reside within open channel 36 of shaft 34 near distal end 38, e.g., adjacent to second incision 72 when attachment feature 29 of lead 16 is placed within hook feature 60. In one example, attachment feature 29 may be placed within hook feature 60 from inside channel 36. In another example, attachment feature 29 may be placed over shaft 34 as the distal end of lead 16 is placed within open channel 36 such that the attachment feature is placed within hook feature 60 from outside of channel 36.

Figure 5D:
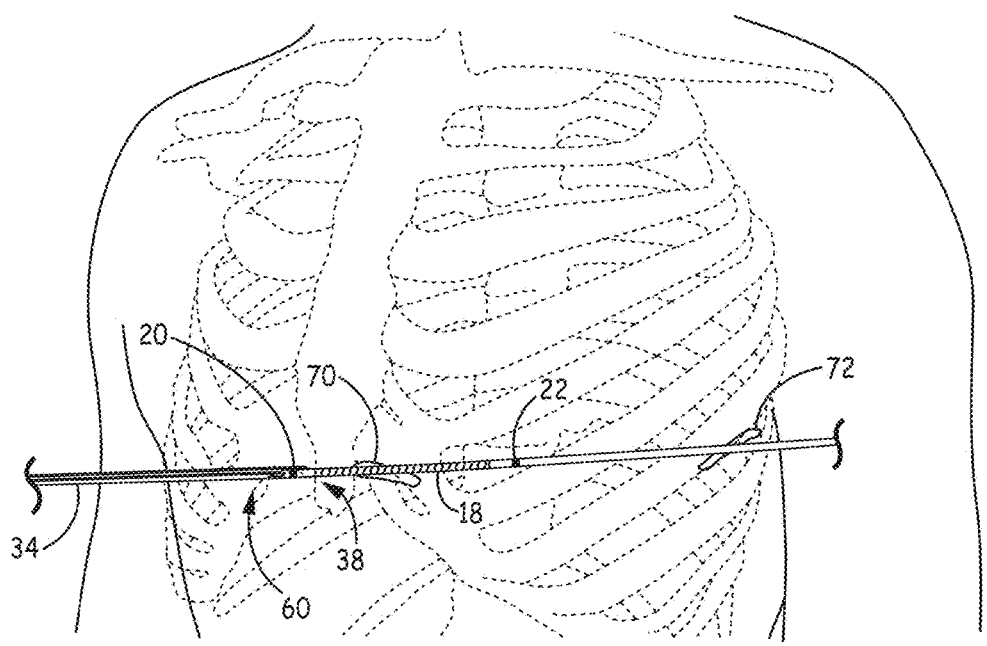

Implant tool 30' is pulled toward first incision 70 pulling lead 16 through the subcutaneous path formed during the previous tunneling of implant tool 30' (as illustrated in FIG. 5D). Defibrillation lead 16 now partially resides within the subcutaneous tissue from first incision 70 to second incision 72 with the distal end of lead 16 extending out of first incision 70 and the proximal end of lead 16 extending out of second incision 72.

The steps illustrated in FIG. 5A-5D are for illustrative purposes only and should not be considered limiting of the techniques described herein. The user may place defibrillation lead 16 along the path from first incision 50 to second incision 52 in other manners. For example, implant tool 30' may be advanced through the subcutaneous tissue from second incision 72 to first incision 70. In this case, an attachment feature of the proximal end of lead 16 may be placed within hook feature 60 and implant tool 30' may be pull lead 16 from incision 70 to incision 72 thereby placing a portion of lead 16 in the subcutaneous path formed during the previous tunneling of implant tool 30'. Alternatively, open channel 36 may be sized to provide an interference fit with a connector of lead 16 or other proximal portion of lead 16 to couple lead 16 to implant tool 30' and allow the user to pull lead 16 from incision 70 to incision 72.

Figure 5E:
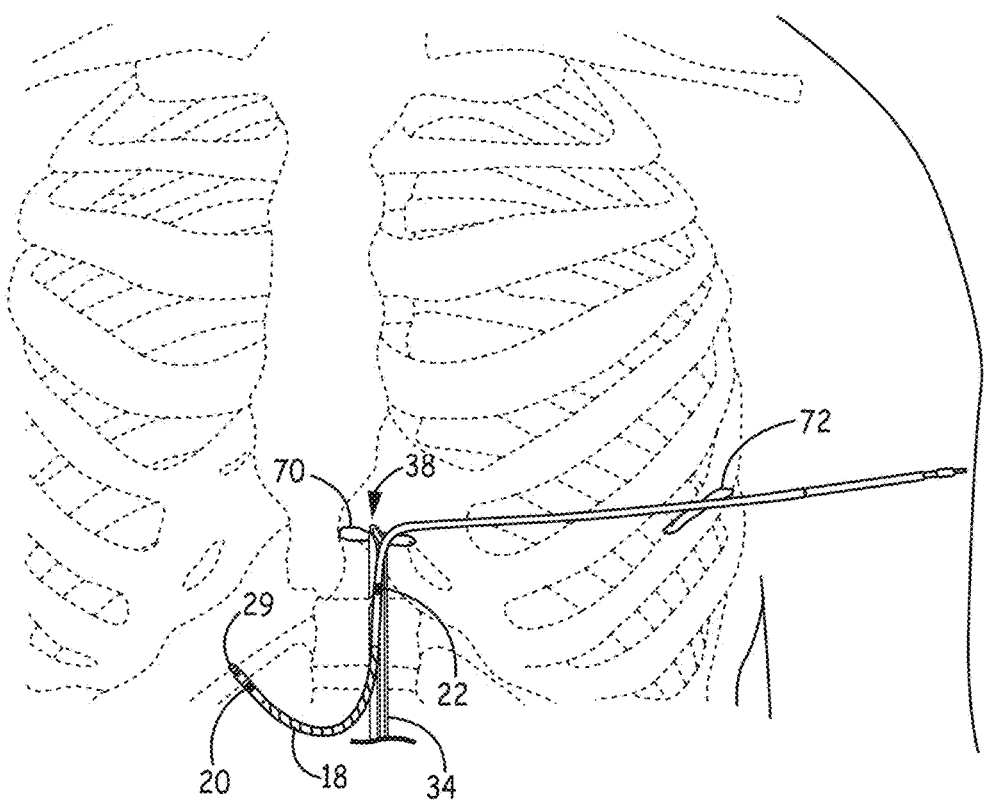
Figure 5F:
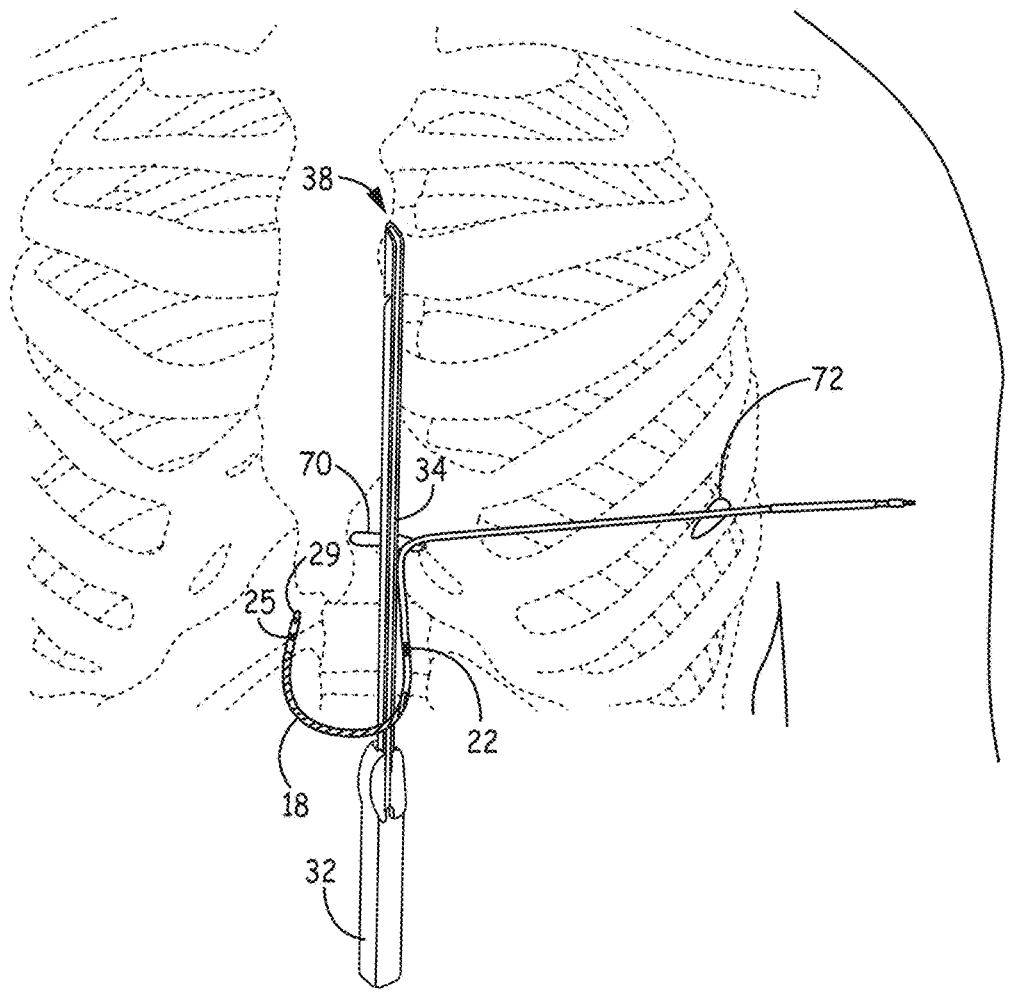

Implant tool 30' is then introduced into first incision 70 near the center of the torso of patient 12 (as illustrated in FIG. 5E). Implant tool 30' is advanced subcutaneously superior from first incision 70 substantially parallel to sternum 28 (as illustrated in FIG. 5F). In the example illustrated in FIG. 5F, the path followed by implant tool 30' is offset laterally to the left of the body of sternum 28 and distal end 38 of implant tool 30' is positioned near the second rib of patient 12. However, implant tool 30' may be advanced along other paths. For example, implant tool 30' may be advanced to create a tunnel or path that is offset from sternum 28 at an angle (e.g., angled lateral from sternum 28 at either the proximal or distal end), is offset from sternum 28 on the right side of sternum 28, over sternum 38, or other path depending on the anatomy of patient 12 and/or location of ICD 14. As another example, distal end 38 of implant tool 30' may be positioned further superior or inferior depending on the location of ICD 14, placement of electrodes 18, 20 and 22 on lead 16, and other factors.

In other examples, implant tool 30' may be introduced into first incision 70 and advanced to create a tunnel or path that is not subcutaneous, but instead is substernal. For example, implant tool 30' may be advanced under/below the sternum and/or ribs. Description of other locations are provided above with respect to FIG. 1.

Figure 5G:
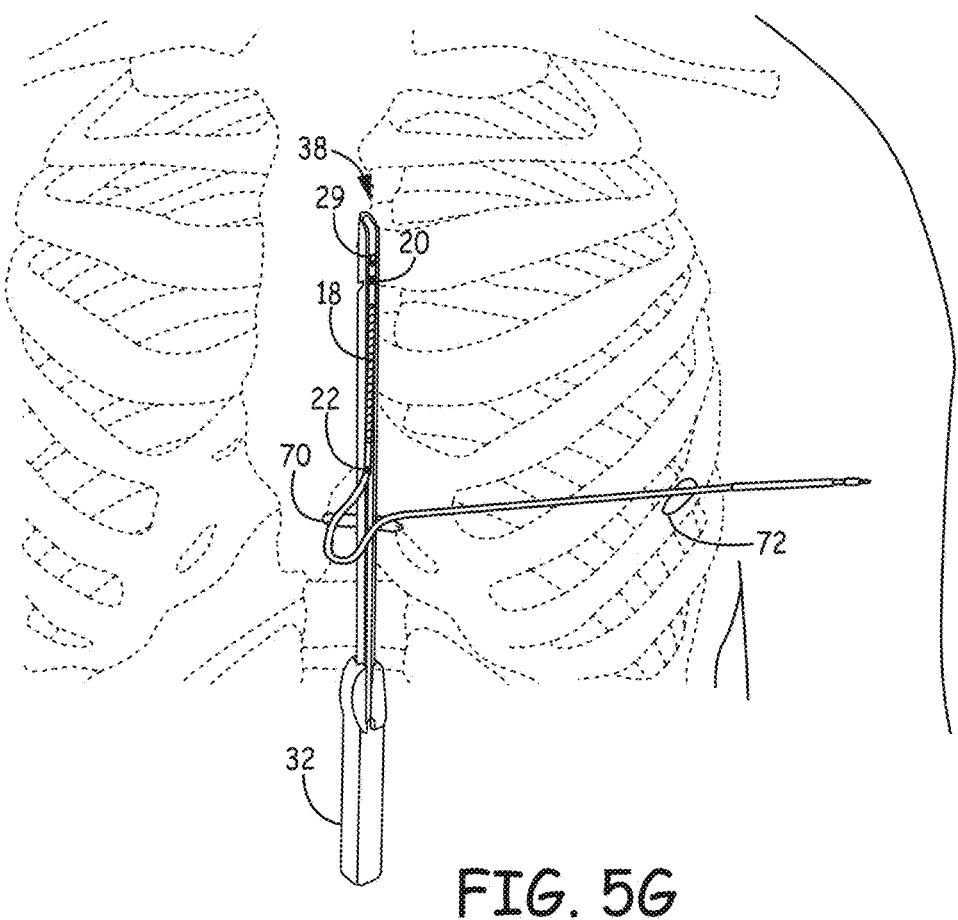

The distal end of lead 16 is introduced into open channel 36 of shaft 34 near first incision 70. In one example, the distal end of lead 16 may be introduced directly into open channel 36. The distal end of defibrillation lead 16 is advanced along open channel 36 from first incision 70 toward distal end 38 of shaft 34 (as illustrated in FIG. 5G). Defibrillation lead 16 will encounter resistance upon reaching distal end 38 of shaft 34 as there is no subcutaneous path past distal end 38 of shaft 34.

Figure 5H:
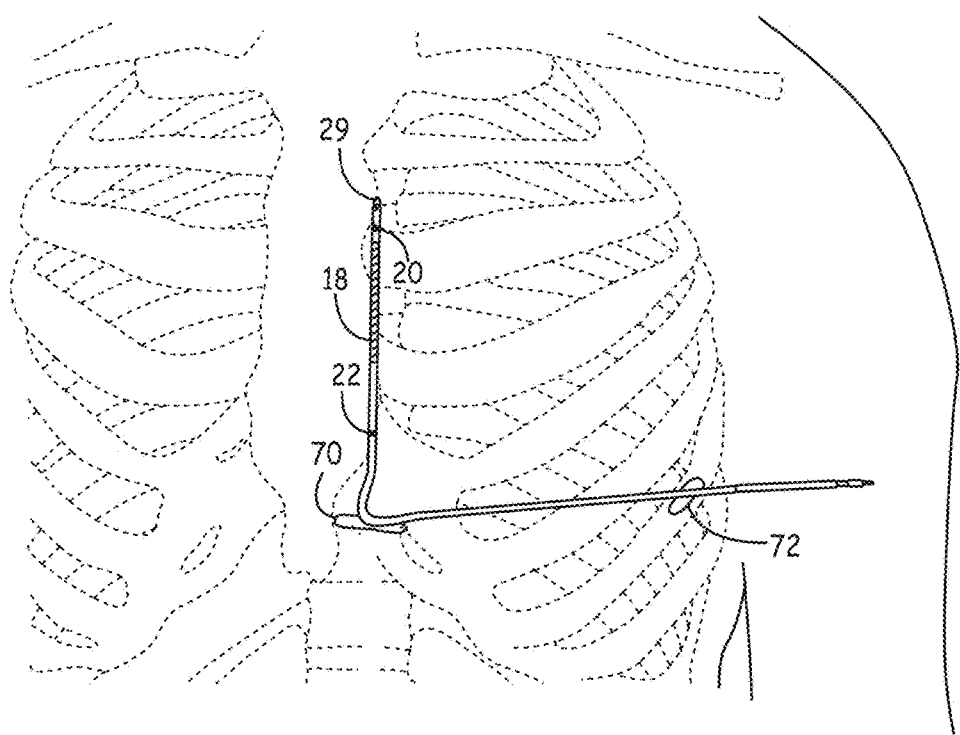

Implant tool 30' is withdrawn toward first incision 70 and removed from the body of patient 12 while leaving defibrillation lead 16 in place (as illustrated in FIG. 5H). In some instances, the distal end of lead 16 may include an anchoring mechanism to fixate the distal end of lead 16 in place near the superior location (e.g., near the second or third rib). The anchoring mechanism may include tines, a helix, or other anchoring mechanisms.

In some instances, a third incision may be made toward the top of sternum 28 proximate the desired location of the distal end of defibrillation lead 16. In this case, implant tool 30' may be advanced subcutaneously from first incision 70 to the third incision until distal end 38 exits through the third incision. The distal end of defibrillation lead 16 would also be advanced through open channel 36 until it is adjacent to the third incision. The distal end of defibrillation lead 16 may then be affixed to the desired location proximate the third incision via a fixation mechanism separate from defibrillation lead 16, e.g., sutures, staples, anchor sleeve, or the like, or built into defibrillation lead 16, e.g., tines, helix or other built in fixation mechanism. Alternatively, implant tool 30' may be advanced from the third incision to first incision 70, attached to lead 16 and withdrawn through the third incision to pull lead 16 along the path from the first to third incision, e.g., in a manner similar to that described in FIGS. 5A-D.

The portion of defibrillation lead 16 proximate first incision 70 may also be affixed to the desired location proximate first incision 70 via a fixation mechanism separate from defibrillation lead 16, e.g., sutures, staples, anchor sleeve, or the like, or built into defibrillation lead 16, e.g., tines, helix, built-in anchor sleeve or other built in fixation mechanism.

A subcutaneous pocket may be created near second incision 72 and ICD 14 may be placed within the subcutaneous pocket. A connector of defibrillation lead 16 is mechanically coupled to the connector block of ICD 14. The various incision and pockets may then be closed to complete the implant procedure.

The example method of implanting a lead illustrated in FIGS. 5A-H is exemplary in nature and should not be considered limiting of the techniques described in this disclosure. Other techniques may be utilized using implant tool 30'. For example, lead 16 may first be implanted along sternum 28 as described in FIGS. 3F-H and then tunneled over to the left side of patient 12, e.g., from incision 70 to incision 72. As another example, instead of advancing implant tool 30' and then pushing lead 16 through open channel 36, lead 16 may be placed within open channel of implant tool 30' prior to introducing lead inserting tool 30' into the incisions such that both the implant tool 30' and lead 16 are tunneled through the tissue at the same time. In a further example, ICD 14 may be placed in the upper right pectoral region and lead 16 may be implanted across the chest and then turn and follow a path inferior along sternum 28. In this example, extravascular ICD system 10 may include a second lead the extends from ICD 14 in the pectoral region along the left side of patient 12 such that an electrode on the second lead may function as an anode or cathode of the therapy vector of such an ICD system.

Figure 6A:
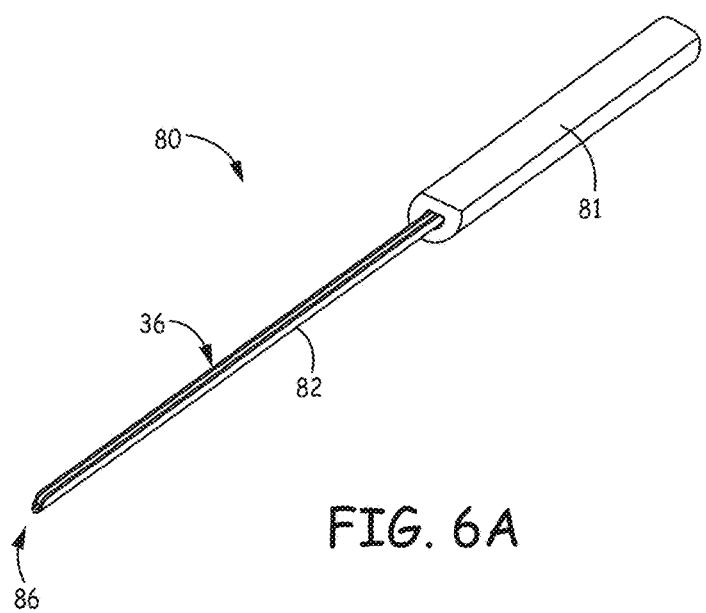

FIG. 6A-6F are schematic diagrams illustrating another implant tool 80. Implant tool 80 can include one or more of the structure and/or functionality of implant tool 30 or 30' of FIGS. 2A-D and FIGS. 4A-D, respectively (and vice versa). Repetitive description of like numbered elements described in other embodiments is omitted for sake of brevity. Implant tool 80 includes a handle 81 and a shaft 82 removably coupled to handle 81, the shaft forming an open channel 36. FIG. 6A is a schematic diagram that illustrates implant tool 80 with shaft 82 coupled to handle 81. FIG. 6B is a schematic diagram that illustrates implant tool 80 with shaft 82 removed from handle 81. FIG. 6C is a schematic diagram that illustrates a cross-sectional view of handle 81 taken from B to B'. FIGS. 6D-6F are schematic diagrams that illustrate various views of shaft 82. FIG. 6G is a cross-sectional view of distal end 86.

As illustrated in FIGS. 6B and 6C, handle 81 may be formed to receive shaft 82. Handle 81 may, for example, include a lumen 83 to receive shaft 82. Lumen 83 may be shaped similar to the outer contour of shaft 82. In the example illustrated in FIG. 7C, lumen 83 is shaped substantially similar to proximal end 84 of shaft 82 illustrated in FIG. 7F. Alternatively, lumen 83 of handle 81 may take on a shape different than the cross-section of shaft 82, but that would interact with shaft 82 to hold shaft 82 in place.

Lumen 83 extends from the distal end of handle 81 toward a proximal end of handle 81. Lumen 83 is configured to couple to the portion of shaft 82 placed within lumen 83, which may be either proximal end 84 and/or distal end 86. Lumen 83 may, for instance, be sized and shaped to provide an interference fit with shaft 82. As described above, the interference fit is achieved by friction after the parts are pushed together, rather than by any other means of fastening. The interference fit may, in some instances, be achieved by sizing and/or shaping the two mating parts so that one or the other, or both, slightly deviate in size from the nominal dimension. The interference fit may therefore be viewed as referring to the fact that one part slightly interferes with the space that the other is taking up. The tightness of the interference fit may be controlled by the amount of allowance, e.g., the planned difference from nominal size. Different allowances will result in various strengths of fit. The value of the allowance depends on which material is being used, how big the parts are, and what degree of tightness is desired.

In one example, lumen 83 may include a tapered portion toward the proximal end of lumen 83 that has a smaller diameter than the outer diameter of proximal end 84 of shaft 82. When proximal end 84 of shaft 82 is pushed within lumen 83 the outer diameter of proximal end 84 of shaft 82 interacts with the wall of lumen 83 at the tapered portion to provide the interference fit. Lumen 83 may likewise be configured to receive distal end 86 of shaft 82 and couple to distal end 86 via an interference fit. Although in the example described with respect to FIG. 6 the coupling is achieved via an interference fit, handle 81 may be coupled to shaft 82 via any of a number of different interlocking mechanisms. Additionally, other techniques for achieving an interference fit may be utilized.

Shaft 82 includes a proximal end 84 and a distal end 86. Distal end 86 may be shaped to aid in tunneling through tissue or muscle. For example, distal end 86 may be tapered, angled, blunt, rounded, pointed or otherwise shaped to enable a user to tunnel through subcutaneous tissue without excess damage to surrounding tissue, piercing through the skin, or coring of the tissue. Distal end 86 may also be shaped to include a bend (e.g., such as bend 110 illustrated in FIG. 11), bulb (e.g., such as bulb 112 illustrated in FIG. 12) or other feature.

Proximal end 84 includes an attachment feature 85 configured to couple to an implantable medical lead, such as lead 16. In the example illustrated in FIGS. 6E and 6F, attachment feature 85 includes a round recess 87 that extends into proximal end 84 and a slit 89 that extends across the diameter and into the proximal end 84. Round recess 87 is sized to interact with a terminal pin of a connector on the proximal end of lead 16. For example, the diameter of recess 87 may be sized to be equal to or slightly smaller than the diameter of the terminal pin of the connector. In this manner, the user of the implant tool may push the terminal pin of the connector of lead 16 into recess 87, which causes slit 89 to slightly expand thereby creating an interference fit with the terminal pin to couple lead 16 to shaft 82. The result is that slit 89 elastically deforms slightly to create a force which results in friction between the terminal pin and the walls forming recess 87.

In some instances, attachment mechanism may form part of the interlocking feature and/or the interference fit. For example, an extension (e.g., similar in size to the terminal pin) may be located within lumen 85 and may interact with attachment mechanism 85 in a similar manner as the terminal pin to provide an interference fit of the handle 81 with the shaft 82. As another example, handle 82 may not include a lumen 85, but instead may include an extension (e.g., similar in size to the terminal pin) that extends from the distal end of handle 81 and interact with attachment mechanism 85 in a similar manner as the terminal pin to provide an interference fit of the handle 81 with the shaft 82.

In other examples, shaft 82 may include a different type of attachment feature near proximal end 84, such as hook feature 60 described above with respect to FIG. 4 or other type of attachment feature. Alternatively, shaft 82 may not include any attachment feature near proximal end 84. In still further examples, shaft 82 may include an attachment feature at or near both proximal end 84 and distal end 86. For instance, shat 82 may include attachment feature 85 at the proximal end 84 and include a hook feature 60 near distal end 86.

Shaft 82 may include any of the variations in thickness described above with respect to shaft 34 of FIG. 2. For example, shaft 82 may have a relatively uniform thickness along the longitudinal length of shaft 82 or varying thickness along the longitudinal length of shaft 82. Likewise, shaft 82 may have a relatively uniform or variable cross-sectional thickness, such as increased thickness on the bottom or side walls of shaft 82 that form open channel 36. Such description of will not be repeated here for sake of brevity.

A user of tool 80 may insert distal end 86 of shaft 82 into an incision and tunnel distal end 86 from a first incision to a second incision (e.g., as described with respect to FIGS. 3A and 3B or FIGS. 5A and 5B). After tunneling distal end 86 of shaft 82 of tool 80, handle 81 of tool 80 may be removed from proximal end 84 of shaft 82 thereby exposing attachment feature 85. An implantable medical lead, such as defibrillation lead 16 of FIG. 1, may be attached to attachment feature 85. In some instances, handle 81 may be placed on the distal end 86 of shaft 82. Whether or not handle 81 is coupled to the distal end 86 of shaft 82, shaft 82 is pulled from the second incision thereby causing lead 16 to be pulled through the tunnel or path formed by implant tool 80. In this case, the entire shaft 82 of implant tool 80 enters the first incision and exist the second incision. In other instances, the implantable electrical lead 16 may be introduced into open channel 36 of shaft 82 and pushed along open channel 36. As such, a user of implant tool 80 may provide the flexibility to implant lead 16 via a variety of different techniques, e.g., via push method, pull method, or a combination of push and pull methods. In some instances, handle 81 may not be utilized at all. In such instances, shaft 82 may be a standalone tool without a removable handle.

Figure 7D:
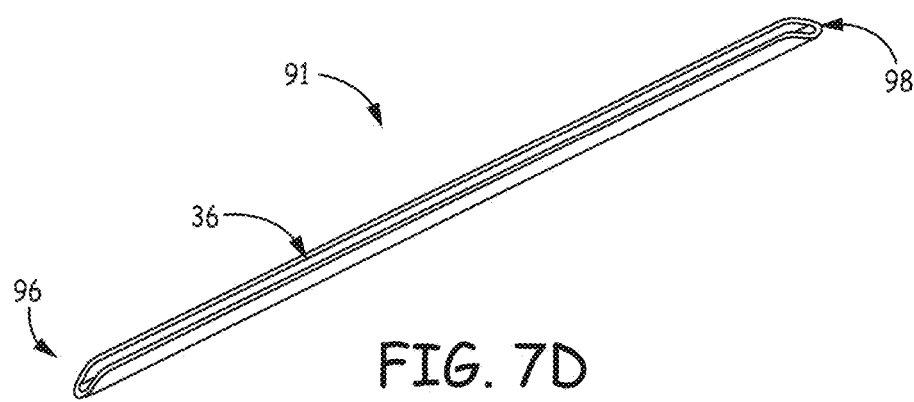
Figure 7E:
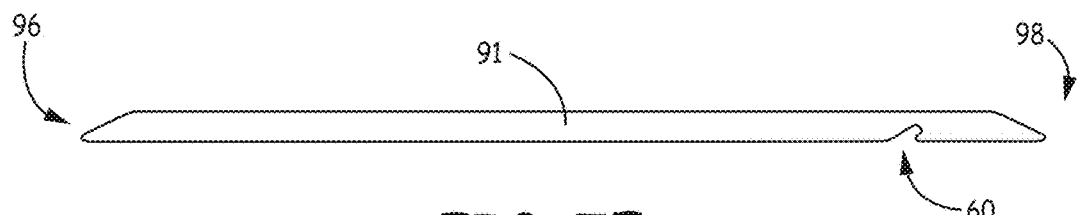
Figure 7F:
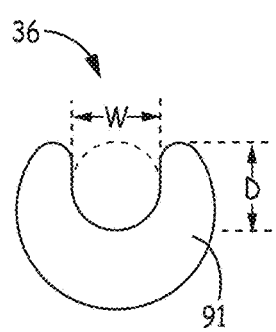
Figure 7G:
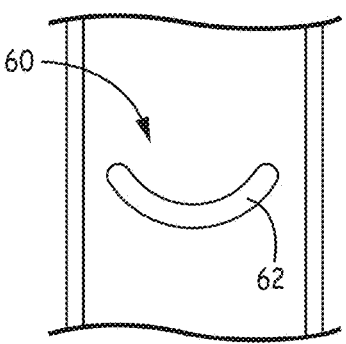

FIG. 7A-7G are schematic diagrams illustrating another example implant tool 90. Implant tool 90 can include one or more of the structure and/or functionality of implant tool 30 of FIGS. 2A-D, implant tool 30' of FIGS. 4A-D, or implant tool 80 of FIGS. 6A-G (and vice versa). Repetitive description of like numbered elements described in other embodiments is omitted for sake of brevity. Implant tool 90 also includes a removable handle 92. FIG. 7A illustrates implant tool 90 with handle 92 attached to shaft 91 and FIG. 7B illustrates implant tool 90 with handle 92 removed from shaft 91. FIG. 7C illustrates a cross-sectional view of handle 92 taken from C-C'. FIG. 7D-7G illustrate various views of shaft 91.

Implant tool 90 includes a shaft 91 having a first end 96 and a second end 98. Shaft 91 includes a hook feature 60 located toward second end 98. Handle 92 may be formed to receive shaft 91. Handle 92 may, for example, include a lumen 94 to receive shaft 91. Lumen 94 may be shaped similar to the outer contour of shaft 91, e.g., as illustrated in FIG. 7C. Alternatively, lumen 94 of handle 92 may take on a shape different than the cross-section of shaft 91, but that would interact with shaft 91 to hold shaft 91 in place. For example, lumen 94 of handle 92 may be semi-circle shaped to accept shaft 91 while leaving channel 36 of the second end 98 of shaft 91 open. Lumen 94 may include a taper or other shape to accommodate a taper or other shape of one or both of end 96 and 98.

In the example illustrated in FIGS. 7A and 7B, handle 92 is sized and shaped to couple to shaft 91. Lumen 94 may, for instance, have a tapered circumference within the lumen 94 to provide an interference fit with shaft 91. In other instances, shaft 91 and handle 92 may each include interlocking mechanisms configured to mate with one another when shaft 91 is inserted within lumen 94 to couple shaft 91 to handle 96. The interlocking mechanisms may be on the portion of shaft 91 that is placed within lumen 94 and on the walls of lumen 94. Alternatively, the interlocking mechanism may be outside of the lumen 94 or a combination thereof. In some instances, hook feature 60 may be the interlocking mechanism or at least part of the interlocking mechanism to couple shaft 91 to handle 92. In instances in which an interlocking mechanism is used instead of an interference fit coupling, shaft 91 may also include an interlocking mechanism toward first end 96 to allow handle 92 may be coupled to either end of shaft 91 depending on whether the user is pushing or pulling the tool.

For example, handle 92 may be attached to end 98 of shaft 91 when the user of implant tool 90 is tunneling through tissue or muscle and placing lead without pulling the lead through the path created via tunneling (e.g., as described with respect to FIGS. 3A-3H and FIGS. 5E-H). Handle 92 may then be removed and reattached to end 96 of shaft 91 to pull the lead through the path created via tunneling (e.g., as described with respect to FIGS. 5C and 5D). In one example, the handle 92 may be removed and reattached to end 96 after tunneling through the tissue and while the shaft 91 remains within patient 12 (e.g., after step 5A and 5B). Alternatively, handle 92 may be removed and reattached to end 96 prior to steps 5A and 5B in which the user is planning on pulling the lead through the path. This provides the user with flexibility in tunneling and implanting a medical electrical lead.

Handle 92 is illustrated as having a grip portion that is offset relative to lumen 94 that receives shaft 91. The offset grip portion may aid the user in tunneling through tissue, muscle, or the like. In other instances, handle 92 may not include and offset grip portion. Instead grip portion may be more in-line with the rest of handle 92 as is the case with handle 82.

Shaft 91 may include any of the variations in thickness described with respect to FIGS. 2, 4 and 9-12. For example, shaft 91 may have a relatively uniform thickness along the longitudinal length of shaft 91 or varying thickness along the longitudinal length of shaft 91. Likewise, shaft 91 may have a relatively uniform or variable cross-sectional thickness, such as increased thickness on the bottom or side walls of shaft 91 that form open channel 36. Likewise, hook feature 60 may include any of the characteristics described above with respect to FIG. 4. Such description of will not be repeated here for sake of brevity.

Figure 8:
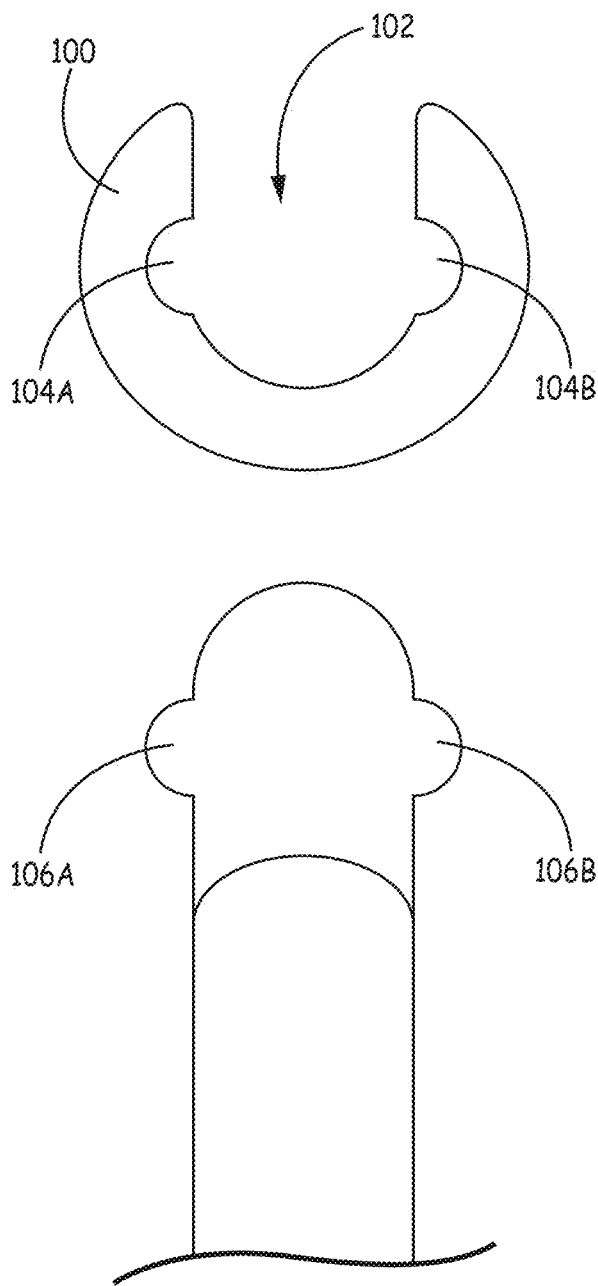
FIG. 8 illustrates a cross-sectional view of an example shaft of an implant tool in conjunction with a distal end of a lead.

FIG. 8 illustrates a cross-sectional view of an example shaft 100 of an implant tool along with a distal end of a lead. Shaft 100 includes an open channel 102 that includes guides 104A and 104B. Shaft 100 can include one or more of the structure and/or functionality of shafts 34, 82 and/or 91 of the embodiments described above. In some instances, the implant tools described above may include one or more features of shaft 100. Repetitive description of like numbered elements described in other embodiments is omitted for sake of brevity.

Guides 104A and 104B extend along an inner surface of the shaft forming open channel 102 from the proximal end of shaft 100 to the distal end of shaft 100. Although in the example illustrated in FIG. 8 shaft 100 includes two guides 104A and 104B, shaft 100 may include only a single guide or more than two guides. Guides 104A and 104B may receive a portion of a lead and guide the lead through open channel 102. In the example illustrated in FIG. 8, a distal end of an example lead is shaped with protrusions 106A and 106B that fit within guides 104A and 104B. In some instances, protrusions 106A and 106B may be part of a fixation mechanism such as tines or a portion of a loop, ring or other distal lead feature. In the case of tines, for example, the tines may deploy upon exiting open channel 102. In addition to or instead of guiding the lead along open channel 102, guides 104A and 104B within open channel 102 may also be useful in orientating lead 16 in a specific direction when placed, e.g., based on how lead 16 is placed within the guides.

Figure 13:
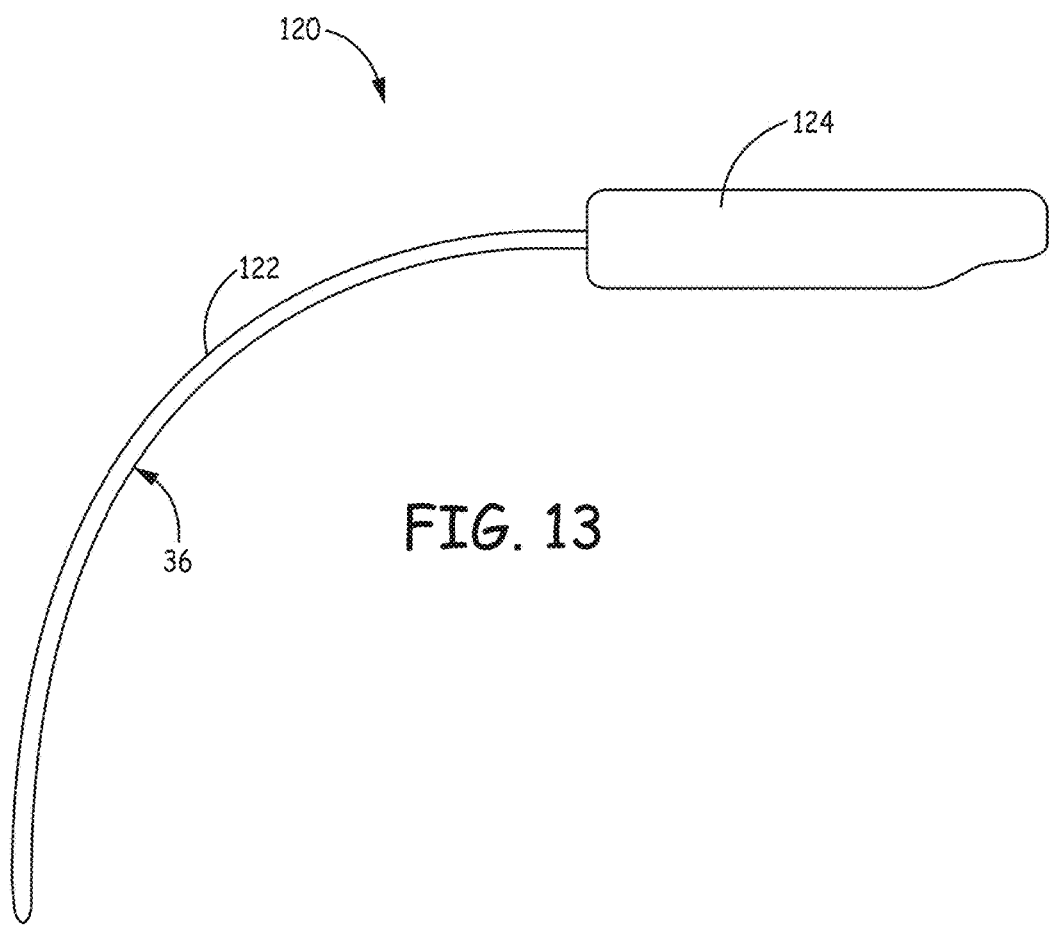
FIG. 13 is a schematic diagram illustrating another example implant tool for implanting a medical lead.

FIG. 13 is a schematic diagram illustrating another example implant tool 120. Implant tool 120 can include one or more of the structure and/or functionality of implant tool 30, 30', 80, 90, or the implant tool of FIG. 8 (and vice versa). Repetitive description of like numbered elements described in other embodiments is omitted for sake of brevity.

Implant tool 120 conforms substantially to implant tool 30, but shaft 122 of implant tool 120 is pre-formed or pre-shaped into the curved shape illustrated in FIG. 13. Shaft 122 may, in one example, have a radius of curvature of between 3 to 5 inches. However, shaft 122 may have a radius of curvature that is greater than 5 inches or less than 3 inches in other embodiments, e.g., depending on the implant procedure for which it will be used. In the example of FIG. 13, open channel 36 is located such that the opening extends along the portion of shaft 122 facing the center of curvature. However, in other instances, open channel 36 may be located such that the opening faces away from the center of curvature or elsewhere.

Figure 14:
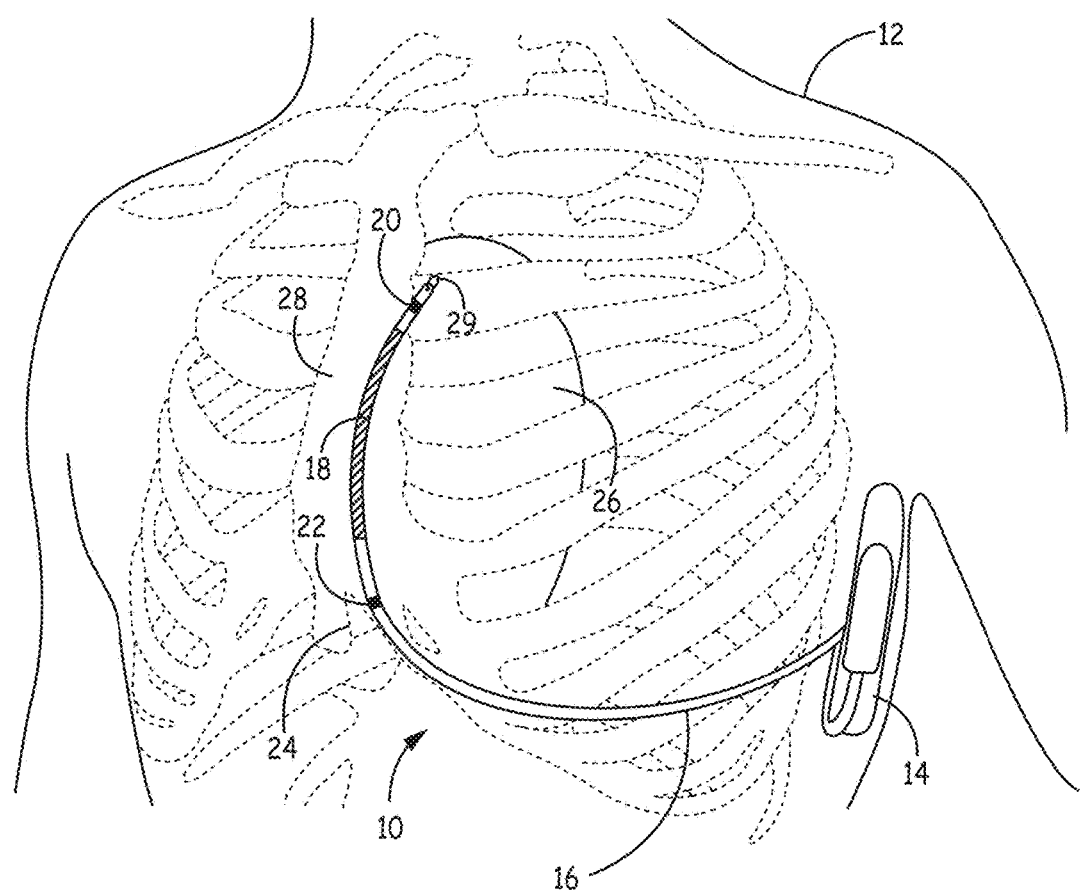
FIG. 14 illustrates a conceptual diagram of a patient implanted with a medical lead using the implant tool illustrated in FIG. 13 and the procedure using a single incision and a single tunnel.

The pre-formed implant tool 120 may allow a user to form a single tunnel from a single incision by advancing implant tool 120 to tunnel a path extending across the torso of the patient and superior along the sternum, advancing lead 16 through open channel 36 of shaft 122, and withdrawing implant tool 120. FIG. 14 illustrates a conceptual diagram of a patient 12 implanted with lead 16 using the implant tool illustrated in FIG. 13 and the procedure using a single incision and a single tunnel described above.

In some instances, handle 124 may be a removable handle (e.g., as described with respect to FIG. 6) and an implant kit may come the handle, a straight shaft (e.g., shaft 82 or 91), and a pre-shaped/pre-formed shaft to provide the user with numerous implant procedure options as the user can use any of the techniques described above to implant defibrillation lead 16.

Figure 15:
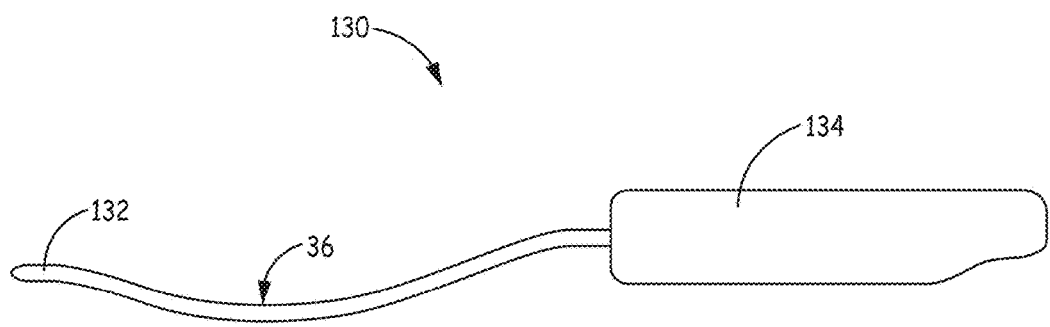
FIG. 15 is a schematic diagram illustrating another example implant tool for implanting a medical lead.

FIG. 15 is a schematic diagram illustrating another example implant tool 130. Implant tool 130 can include one or more of the structure and/or functionality of implant tool 30, 30', 80, 90, the implant tool of FIG. 8, and/or implant tool 120 (and vice versa). Repetitive description of like numbered elements described in other embodiments is omitted for sake of brevity.

Implant tool 120 conforms substantially to implant tool 30, but shaft 132 has a slight bend as illustrated in FIG. 15.

The bend or curvature of shaft 132 may be particularly useful for tunneling underneath/below the sternum. In particular, the bend or curvature of shaft 132 orients the distal end of shaft 132 toward sternum thereby keeping the distal end away from organs in the body cavity during tunneling through the substernal space. Open channel 36 is illustrated as opening toward the underside of the sternum. In other instances, however, open channel 36 may open away from the sternum or in another direction.

Although not illustrated in FIG. 15, the distal end of shaft 132 may include an atraumatic tip constructed of a low durometer, flexible material (such as silicone) to reduce the likelihood of puncturing or otherwise damaging the pleura and/or pericardium or others structure in those locations. In some instances, the atraumatic tip may include radiopaque markers or the low durometer, flexible material may include a radiopaque additive to allow visualization of the distal end of shaft 132. For example, fluoroscopy may be used to determine the shape and deflection of the distal end of shaft 132 during tunneling.

Various examples have been described. These and other examples are within the scope of the following claims.

The invention claimed is:

1. An implant tool for implanting a medical lead, the implant tool comprising:
   a shaft having a proximal end and a distal end, wherein the shaft includes:
      an open channel that extends from near the proximal end to the distal end of the shaft, wherein a thickness of a wall along the bottom of the shaft below the open channel is substantially uniform and the thickness is configured such that the open channel is offset from a central longitudinal axis of the shaft; and
      an attachment feature configured to couple to the medical lead.

2. The implant tool of claim 1, further comprising a handle adjacent to the shaft.

3. The implant tool of claim 2, wherein the handle is removable from the shaft.

4. The implant tool of claim 3, wherein the handle is configured to couple directly to at least one of the proximal end of the shaft and the distal end of the shaft.

5. The implant tool of claim 2, wherein the handle includes a lumen configured to receive a portion of the shaft, the lumen and shaft creating an interference fit that couples the shaft to the handle, wherein the interference fit is at an interface between the shaft and a surface of the handle defining the lumen.

6. The implant tool of claim 2, wherein the handle includes a lumen that extends only partially through the handle, wherein the lumen is configured to receive at least one of the proximal end of the shaft and the distal end of the shaft within the lumen to couple the shaft to the handle.

7. The implant tool of claim 2, wherein the handle and shaft are configured such that when the handle is coupled and adjacent to the shaft, the open channel of the shaft is not covered.

8. The implant tool of claim 5, wherein one of the distal end or proximately end of the shaft is configured to be located within the handle when the interference fit couple the shaft to the handle.

9. The implant tool of claim 1, wherein the attachment feature comprises a hook feature located along an inner surface of the shaft between the distal end and the proximal end of the shaft that is opposite an opening of the channel, the hook feature being configured to couple to a feature of the medical lead.

10. The implant tool of claim 9, wherein the shaft has a thickness and the hook feature extends through the thickness of the shaft such that there is an opening through the surface of the shaft between the distal end and the proximal end of the shaft.

11. The implant tool of claim 9, wherein the shaft has a thickness and the hook feature does not extend through the thickness of the shaft.

12. The implant tool of claim 1, wherein the attachment feature comprises a round recess that extends into the proximal end of the shaft, wherein the recess is sized to receive and couple to a portion of the medical lead.

13. The implant tool of claim 12, wherein the recess is sized to receive and couple to a terminal pin of a connector on the proximal end of the medical lead.

14. The implant too of claim 12, wherein the attachment feature further comprises a slit that extends across the diameter of the proximal end of the shaft and into the proximal end of the shaft.

15. The implant tool of claim 12, wherein the recess of the proximal end of the shaft and the portion of the medical lead are coupled via an interference fit.

16. The implant tool of claim 1, wherein the open channel includes at least one guide along an inner surface of the shaft forming the open channel, the guide being configured to receive a portion of an implantable medical lead.

17. The implant tool claim 1, wherein the shaft includes a plurality of markings that identify locations that coincide with locations of features of the medical lead when the medical lead is placed within the open channel such that a distal end of the lead is located at the distal end of the shaft.

18. The implant tool of claim 17, wherein the markings identify locations that coincide with locations of electrodes of the medical lead when the medical lead is placed within the open channel such that the distal end of the lead is located at the distal end of the shaft.

19. The implant tool of claim 1, wherein the implant tool is formed of at least one of a molded polymer and a metal.

20. The implant tool of claim 1, wherein a thickness of a wall of the shaft is uniform along a length of the shaft from the proximal end to the distal end.

21. The implant tool of claim 1, wherein a first thickness of a wall of the shaft toward the distal end is not substantially the same as a second thickness of the wall the shaft at the proximal end.

22. The implant tool of claim 1, wherein a first thickness of a wall of the shaft along sides of the shaft forming the open channel is less than the thickness of the shaft wall along the bottom of the shaft below the open channel.

23. The implant tool of claim 1, wherein the shaft is a curved shaft, the curved shaft having a radius of curvature of between three (3) and five (5) inches.

24. The implant tool of claim 1, wherein the distal end of the shaft includes a rounded edge.

25. The implant tool of claim 1, wherein the open channel includes at least one guide along an inner surface of the shaft forming the open channel, the guide being recessed into the inner surface of the shaft and configured to receive a protrusion portion of an implantable medical lead within the recess of the guide to guide the lead within the open channel.

26. The implant tool of claim 1, wherein the open channel is offset from the central longitudinal axis of the shaft such that a central longitudinal axis of the open channel is above the central longitudinal axis of the shaft relative the bottom wall of the open channel.

27. The implant tool of claim 1, wherein the open channel is offset from the central longitudinal axis of the shaft such that a central longitudinal axis of the open channel is below the central longitudinal axis of the shaft relative the bottom wall of the open channel.

28. An implant tool system for implanting a medical lead, the implant tool system comprising:
the medical lead; and
an implant tool comprising a shaft having a proximal end and a distal end, wherein the shaft includes an open channel that extends from near the proximal end to the distal end of the shaft, wherein a thickness of a wall along the bottom of the shaft below the open channel is substantially uniform and the thickness is configured such that the open channel is offset from a longitudinal axis of the shaft.

29. The system of claim 28, wherein the open channel has a width that is greater than or equal to an outer diameter of the medical lead.

30. The system of claim 29, wherein the open channel further includes a depth that is greater than or equal to the outer diameter of the medical lead.

31. The system of claim 28, wherein a width of the open channel is approximately equal to an outer diameter of the medical lead at a location along a length of the medical lead such that when the medical lead is placed within the open channel there is an interference fit between the shaft and the medical lead at the location.

32. The system of claim 28, further comprising an attachment feature, wherein the attachment feature comprises a round recess that extends into the proximal end of the shaft, wherein the recess is sized to receive and couple to a portion of the medical lead.

33. The system of claim 32, wherein the recess is sized to receive and couple to a terminal pin of a connector on the proximal end of the medical lead.

34. The system of claim 32, wherein the recess of the proximal end of the shaft and the portion of the medical lead are coupled via an interference fit.

* * * * *